US012573484B2

(12) United States Patent　　　　(10) Patent No.:　US 12,573,484 B2
　Chang et al.　　　　　　　　　　　(45) Date of Patent:　　Mar. 10, 2026

(54) SYSTEM AND METHOD FOR AUTOMATICALLY DISPLAYING INFORMATION AT A RADIOLOGIST DASHBOARD

(71) Applicant: RAD AI, Inc., San Francisco, CA (US)

(72) Inventors: Jeffrey Chang, Berkeley, CA (US); Doktor Gurson, Berkeley, CA (US)

(73) Assignee: RAD AI, Inc., San Francisco, CA (US)

( * ) Notice: Subject to any disclaimer, the term of this patent is extended or adjusted under 35 U.S.C. 154(b) by 0 days.

(21) Appl. No.: 18/952,147

(22) Filed: Nov. 19, 2024

(65) Prior Publication Data

US 2025/0166763 A1　　May 22, 2025

Related U.S. Application Data

(60) Provisional application No. 63/602,073, filed on Nov. 22, 2023.

(51) Int. Cl.
　G16H 15/00　　　(2018.01)
　G06F 40/40　　　(2020.01)
　G16H 10/60　　　(2018.01)
(52) U.S. Cl.
　CPC ................................. G16H 15/00 (2018.01)
(58) Field of Classification Search
　CPC ...................................................... G16H 15/00
　See application file for complete search history.

(56) References Cited

U.S. PATENT DOCUMENTS

| | | | |
|---|---|---|---|
| 10,395,772 | B1 | 8/2019 | Lucas et al. |
| 10,667,794 | B2 | 6/2020 | Beymer et al. |
| 11,064,902 | B2 | 7/2021 | Wallace et al. |
| 11,069,432 | B2 | 7/2021 | Guo et al. |
| 11,263,749 | B1 | 3/2022 | Purushottam et al. |
| 11,380,432 | B2 | 7/2022 | Glottmann et al. |
| 11,403,786 | B2 | 8/2022 | Farri et al. |
| 11,803,759 | B2 | 10/2023 | Hu et al. |
| 11,961,624 | B2 | 4/2024 | Smurro |
| 12,032,658 | B2 | 7/2024 | Kiraly et al. |
| 2018/0322254 | A1 | 11/2018 | Smurro |

(Continued)

FOREIGN PATENT DOCUMENTS

| | | |
|---|---|---|
| CN | 116364227 A | 6/2023 |
| CN | 117558439 A | 2/2024 |

(Continued)

OTHER PUBLICATIONS

Chang, Jeffrey , et al., "Method and System for the Computer-Aided Processing of Medical Images", U.S. Appl. No. 18/952,233, filed Nov. 19, 2024.

(Continued)

*Primary Examiner* — Maroun P Kanaan
(74) *Attorney, Agent, or Firm* — Jeffrey Schox

(57)　　　　　ABSTRACT
Embodiments of systems and methods for dynamic and/or live retrieval and display of relevant clinical outputs to a clinical entity are provided, for a clinical entity processing a case. The systems and methods leverage advanced models (e.g., multimodal models) for retrieval, processing, and rendering of relevant information to the clinical entity, in a manner that improves worklist processing performance. Application areas include systems and tools for radiologists.

17 Claims, 9 Drawing Sheets

(56) References Cited

U.S. PATENT DOCUMENTS

| | | | | |
|---|---|---|---|---|
| 2020/0334416 A1 | 10/2020 | Vianu et al. | | |
| 2020/0380675 A1 | 12/2020 | Golden et al. | | |
| 2021/0216822 A1* | 7/2021 | Paik | ..................... | G16H 15/00 |
| 2022/0254464 A1* | 8/2022 | Pinto | ..................... | G16H 15/00 |
| 2023/0051982 A1* | 2/2023 | Sasidharan | ........... | G16H 15/00 |
| 2023/0079929 A1 | 3/2023 | Bradski et al. | | |
| 2023/0197276 A1 | 6/2023 | Chang et al. | | |
| 2024/0266074 A1 | 8/2024 | Smurro | | |
| 2024/0329795 A1* | 10/2024 | Dehkordi | ............... | G06F 3/011 |
| 2024/0347156 A1 | 10/2024 | Paulett et al. | | |

FOREIGN PATENT DOCUMENTS

| | | |
|---|---|---|
| CN | 117995344 A | 5/2024 |
| CN | 118070227 A | 5/2024 |

OTHER PUBLICATIONS

Xu, Shawn , et al., "ELIXR: Towards a general purpose X-ray artificial intelligence system through alignment of large language models and radiology vision encoders", arXiv:2308.01317 [cs.CV], Aug. 2, 2023.
Li, Junnan , et al., "BLIP-2: Bootstrapping Language-Image Pre-training with Frozen Image Encoders and Large Language Models", arXiv:2301.12597v1, Jan. 30, 2023.

* cited by examiner

Current
study

Current
study

S22a

S22b

Second Stage of Training

Second Stage of Inference

Phase 1 Inference

Phase 2 Inference

SYSTEM AND METHOD FOR AUTOMATICALLY DISPLAYING INFORMATION AT A RADIOLOGIST DASHBOARD

CROSS-REFERENCE TO RELATED APPLICATIONS

This application claims the benefit of U.S. Provisional Application No. 63/602,073, filed 22 Nov. 2023, which is incorporated in its entirety by this reference.

TECHNICAL FIELD

This invention relates generally to the radiology field, and more specifically to a new and useful system and method for dynamically rendering information at a radiologist dashboard in the radiology field.

DETAILED DESCRIPTION

The following description of the embodiments of the invention is not intended to limit the invention to these embodiments, but rather to enable any person skilled in the art to make and use this invention.

1. OVERVIEW

Figure 1A:
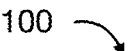
FIG. 1A is a schematic representation of an embodiment of a method for dynamic retrieval and transmission of information.
Figure 1A:
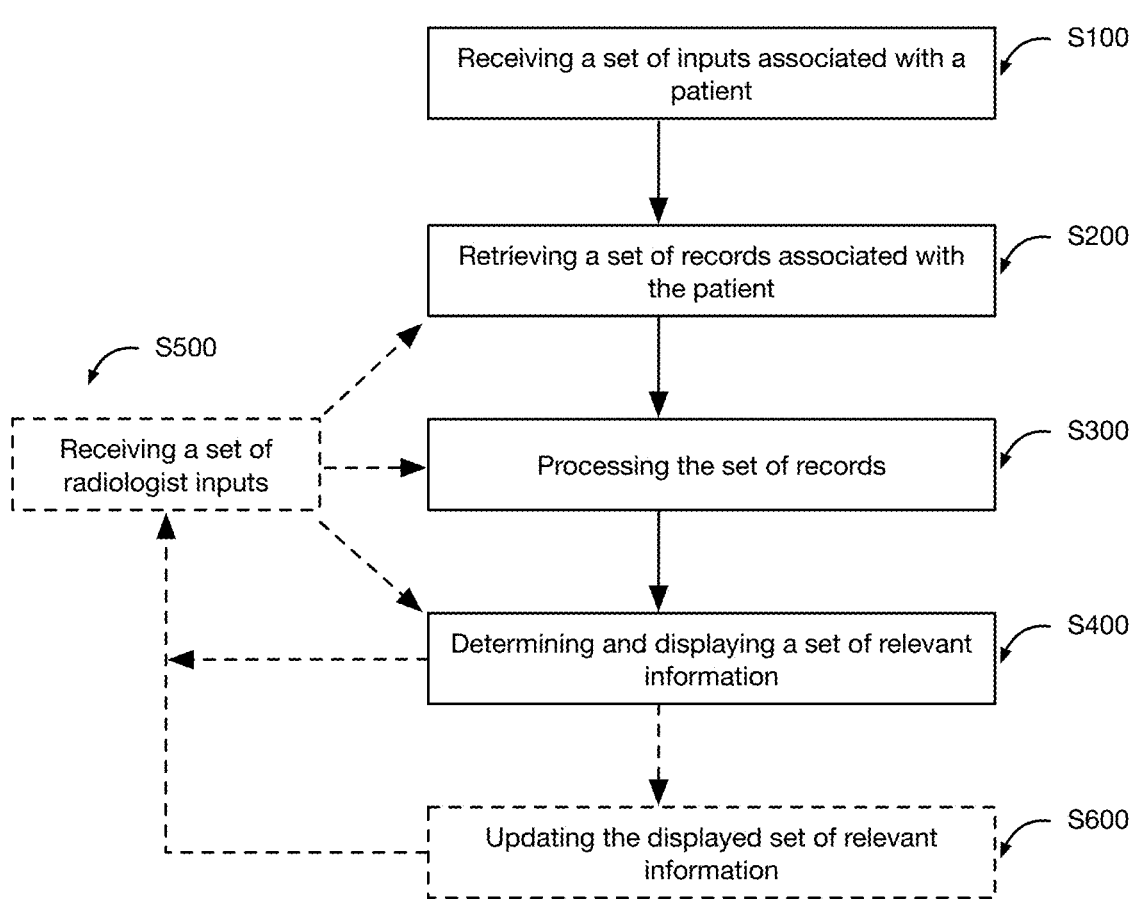

As shown in FIG. 1A, a method 100 for displaying information at a radiologist dashboard can include: receiving a set of inputs associated with a patient S100, retrieving a set of records associated with the patient S200, processing the set of records S300, determining and displaying a set of relevant information S400, optionally receiving a set of radiologist inputs S500, optionally updating the displayed set of relevant information S600, and/or any other suitable steps.

Figure 1B:
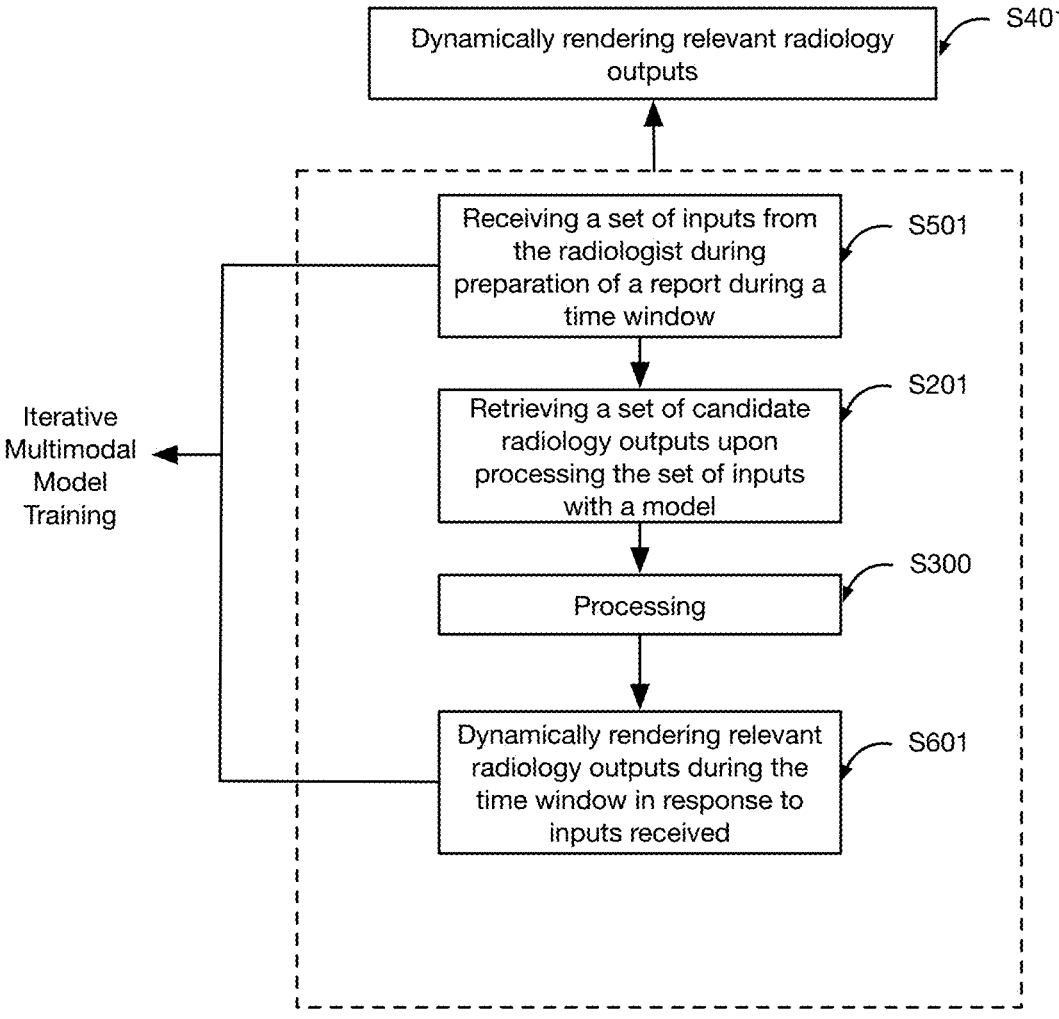
FIG. 1B is a schematic representation of an embodiment of a method for dynamic retrieval and transmission of information.

A variation of method 100 can include additional steps, where, as shown in FIG. 1B, a method can include: at a panel of a display of a platform for radiology report generation, dynamically rendering relevant radiology outputs of a set of candidate radiology outputs, to a radiologist in response to receiving a set of inputs from the radiologist S401, wherein dynamically rendering relevant radiology outputs includes: at a computing system of the platform, receiving the set of inputs from the radiologist, the set of inputs associated with a session with a patient, and the set of inputs received during a time window as the radiologist is preparing a report using the platform S501; retrieving a set of candidate radiology outputs upon processing the set of inputs with the multimodal model, during the time window S201; dynamically rendering relevant radiology outputs of the set of candidate radiology outputs at the panel of a display, wherein dynamically rendering comprises adjusting display of relevant radiology outputs at the panel during the time window, as the radiologist provides the set of inputs during the time window S601.

In variants, the method can function to provide relevant and/or customized information to radiologists regarding a case that is currently being reviewed (e.g., in the context of report generation, in the context of review of radiology findings).

However, the method can be otherwise performed.

2. TECHNICAL ADVANTAGES

Variants of the technology for displaying information at a radiologist dashboard can confer several benefits over conventional systems and methods.

First, by automatically searching through a patient's medical records to retrieve and display relevant information, variants of the technology can enable users (e.g., radiologists) to find key information relevant to a particular case more easily (e.g., faster, with less manual effort) and thoroughly (e.g., additionally increase a radiologist's throughput). In conventional radiology workflows, radiologists must often manually parse through one or more records for a case (e.g., prior reports, images, laboratory tests, notes, etc.) to search for relevant information (e.g., specifies lab values, family history, etc.), possibly across multiple systems (e.g., EHR systems), which can lead them to miss critical information within a patient's records, particularly if they do not know what information to search for. As such, the technology confers the benefit of decreasing the time, effort, and/or workload involved in a radiologist completing a radiology report or processing/reviewing other radiology or clinical information, through the automation of any or all processes involved. This can further enable any or all of: additional time for the radiologist to perform complex analyses, additional reports that the radiologist can analyze in a set period of time, a decrease in a number of radiologists needed at certain points of time (e.g., undesirable hours, surges in cases, etc.), and/or any other outcomes. Exemplary performance improvements attributed to the systems and methods described are provided below.

In one specific use case, the technology can automatically detect the organ or specific lesion/mass that a radiologist is currently reviewing in images, based upon inputs received from the radiologist, where exemplary inputs can include one or more of: mouse movement, mouse location, cursor movement, cursor location, annotations or measurements the radiologist is providing either automatically or manually, working progress on a section of the radiology report template that the radiologist's caret is currently in within the reporting platform, inputs generated from eye tracking systems, inputs generated from face-tracking systems, dictated inputs, and other inputs. The inputs are then processed according to methods described, to automatically provide real-time updating of the dashboard. Updated dashboard renderings can include summarizations of findings from the prior report(s), renderings automatically comparing mass/lesion evolution in morphology or other parameters over multiple studies (e.g., based on automatically measuring the mass/lesion in prior imaging studies, based on the description of mass/lesion size in prior reports, etc.), retrieved relevant labs for a particular organ system (LFTs when assessing the liver, pancreatic labs when assessing the pancreas, etc.), and/or other retrieved information.

Second, automatically retrieving relevant information from a patient's medical history can further prevent the recommendation of unnecessary follow-ups (e.g., laboratory tests, exams, visits, etc.) by radiologists (e.g., by flagging a prior follow-up) by surfacing the patient's history that would contraindicate the necessity of a follow-up.

Third, automatically retrieving relevant information from a patient's medical history can improve an accuracy of a diagnosis and/or a patient outcome by helping radiologists find information they could have missed otherwise.

Fourth, variants of the technology can enable radiologists to make narrower diagnoses than would be possible given radiologists' limited time and/or resources (e.g., access to a particular EHR system) to review a patient's entire medical history. The method can include detecting and displaying information relevant to a differential diagnosis (e.g., patient information, example findings for each of the differentials, etc.) that can help the radiologist further narrow the diagnosis.

Fifth, variants of the technology can increase a uniformity and/or consistency among radiologist outcomes.

However, the technology can confer any other suitable benefits.

3. SYSTEM

Figure 2A:
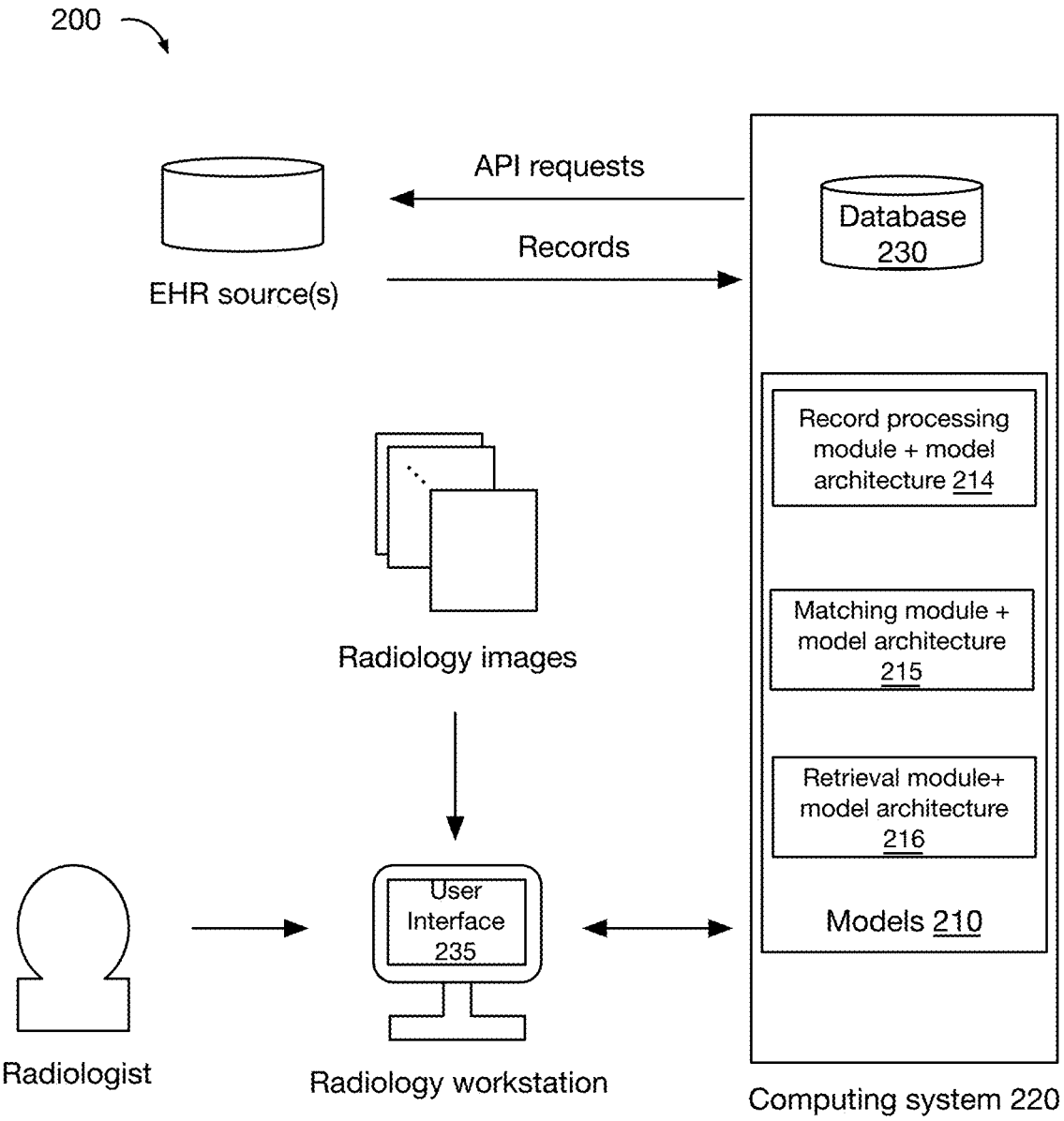
FIG. 2A is a schematic representation of an embodiment of a system for dynamic retrieval and transmission of information.
Figure 2B:
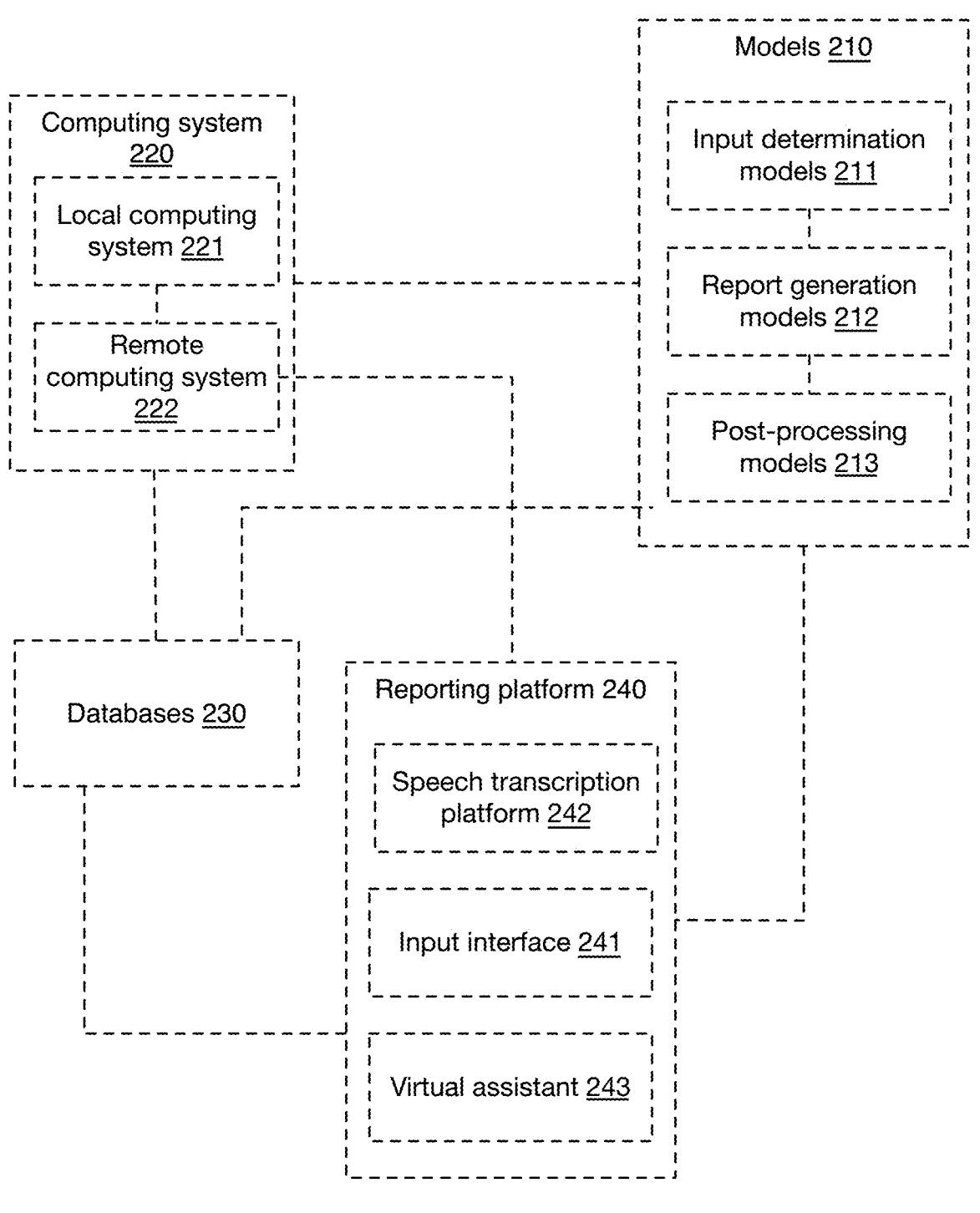
FIG. 2B is a schematic representation of an embodiment of a system for dynamic retrieval and transmission of information.

As shown in FIGS. 2A and 2B, an embodiment of a system 200 can include and/or interface with any or all of: one or more models/modules 210, a computing system 220, a database 230, a user interface (e.g., a radiology dashboard 235), user devices (e.g., a radiology workstation), and/or any other suitable system components. As shown in FIG. 2B, the system 100 can include and/or interface with any or all of: one or more models 210, a computing system 220, a set of databases 230, a user interface (e.g., referred to equivalently herein as an "input interface"), a reporting platform 240, user devices, and/or any other suitable system components.

Additionally or alternatively, the system can include any or all of the components as described in any or all of: U.S. application Ser. No. 16/688,623, filed 19 Nov. 2019; U.S. application Ser. No. 17/020,593, filed 14 Sep. 2020; U.S. application Ser. No. 17/690,751, filed 9 Mar. 2022; U.S. application Ser. No. 18/215,354, filed 28 Jun. 2023; U.S. application Ser. No. 17/649,213, filed 28 Jan. 2022; U.S. application Ser. No. 18/374,535, filed 28 Sep. 2023; and U.S. application Ser. No. 18/374,526, filed 28 Sep. 2023, each of which is incorporated in its entirety by this reference.

The system is preferably used by a radiologist, but can additionally or alternatively be used by any medical professional (e.g., physician, specialist, nurse, etc.), a patient (e.g., wherein the system is configured to display relevant information in a patient's history to the patient alongside their images), and/or any other suitable user. As referred to herein, "user" and "radiologist" can be used interchangeably, but other users can be understood to use the system.

The system 100 functions to automatically retrieve and render radiology information to a clinical entity (e.g., radiologist) that can be utilized (e.g., by a radiologist, by additional automated processes, etc.) to increase radiology workflow efficiency. Additionally or alternatively, the system 100 can function to: increase an accuracy, comprehensiveness, or other metric(s) of a produced radiology report, by dynamically informing a radiologist with relevant information as they prepare reports and/or review information (e.g., findings, images); produce an entire radiology report and/or preliminary radiology report (e.g., radiology report without impression section, draft radiology report, etc.); and/or otherwise suitably function.

In embodiments, variations, and examples, the system 100 includes multimodal vision model and large language model (LLM) architecture that can improve functionality of radiology systems (e.g., radiology report systems) that support radiologists in processing their respective worklists, in relation to workflow performance enhancements.

In examples, increased efficiency/speed performance can be attributed to the system 200 and methods 100 described, whereby increased speed performance can include: 30 minutes saved (e.g., per clinical shift, per caretaking shift, per radiologist shift), thus providing ~6% improved speed in relation to standard systems; 35 minutes saved (e.g., per clinical shift, per caretaking shift, per radiologist shift), thus providing ~7% improved speed in relation to standard systems; 40 minutes saved (e.g., per clinical shift, per caretaking shift, per radiologist shift), thus providing ~8% improved speed in relation to standard systems; 45 minutes saved (e.g., per clinical shift, per caretaking shift, per radiologist shift), thus providing ~9% improved speed in relation to standard systems; 50 minutes saved (e.g., per clinical shift, per caretaking shift, per radiologist shift), thus providing ~10% improved speed in relation to standard systems; 55 minutes saved (e.g., per clinical shift, per caretaking shift, per radiologist shift), thus providing ~11% improved speed in relation to standard systems; 60 minutes saved (e.g., per clinical shift, per caretaking shift, per radiologist shift), thus providing ~12% improved speed in relation to standard systems; 65 minutes saved (e.g., per clinical shift, per caretaking shift, per radiologist shift), thus providing ~13% improved speed in relation to standard systems; 70 minutes saved (e.g., per clinical shift, per caretaking shift, per radiologist shift), thus providing ~14% improved speed in relation to standard systems; 75 minutes saved (e.g., per clinical shift, per caretaking shift, per radiologist shift), thus providing ~15% improved speed in relation to standard systems; 80 minutes saved (e.g., per clinical shift, per caretaking shift, per radiologist shift), thus providing ~16% improved speed in relation to standard systems; or greater speed performance.

In examples, detection sensitivity performance is also attributed to the systems 200 and methods 100 described. In examples, the system 100 provided: greater than 70% sensitivity (e.g., in detection of a clinical indication, such as an intracranial hemorrhage), greater than 71% sensitivity (e.g., in detection of a clinical indication, such as an intracranial hemorrhage), greater than 72% sensitivity (e.g., in detection of a clinical indication, such as an intracranial hemorrhage), greater than 73% sensitivity (e.g., in detection of a clinical indication, such as an intracranial hemorrhage), greater than 74% sensitivity (e.g., in detection of a clinical indication, such as an intracranial hemorrhage), greater than 75% sensitivity (e.g., in detection of a clinical indication, such as an intracranial hemorrhage), greater than 76% sensitivity (e.g., in detection of a clinical indication, such as an intracranial hemorrhage), greater than 77% sensitivity (e.g., in detection of a clinical indication, such as an intracranial hemorrhage), greater than 78% sensitivity (e.g., in detection of a clinical indication, such as an intracranial hemorrhage), greater than 79% sensitivity (e.g., in detection of a clinical indication, such as an intracranial hemorrhage), greater than 80% sensitivity (e.g., in detection of a clinical indication, such as an intracranial hemorrhage), greater than 85% sensitivity (e.g., in detection of a clinical indication, such as an intracranial hemorrhage), greater than 90% sensitivity (e.g., in detection of a clinical indication, such as an intracranial hemorrhage), or greater sensitivity.

In examples, detection specificity performance is also attributed to the system 100. In examples, the system 100 provided: greater than 80% specificity (e.g., in detection of a clinical indication/anomaly), greater than 82% specificity (e.g., in detection of a clinical indication/anomaly), greater than 84% specificity (e.g., in detection of a clinical indication/anomaly), greater than 86% specificity (e.g., in detection of a clinical indication/anomaly), greater than 88% specificity (e.g., in detection of a clinical indication/anomaly), greater than 90% specificity (e.g., in detection of a clinical indication/anomaly), greater than 92% specificity (e.g., in detection of a clinical indication/anomaly), greater than 94% specificity (e.g., in detection of a clinical indication/anomaly), greater than 96% specificity (e.g., in detection of a clinical indication/anomaly), greater than 98% specificity (e.g., in detection of a clinical indication/anomaly), or greater specificity. Specificity can be determined based upon determination of false positive and/or false negative metrics, with respect to anomaly detection/clinical indication detection according to methods described, and involving use of systems described.

As shown in FIGS. 2A and 2B, the system 200 includes a set of models 110, which function to perform any or all of the processing, generation, training, re-training, transmission, action execution, and/or other steps in the methods 100 (e.g., as described below). Variations of models can include input determination models 211, report generation models 212 (e.g., language model), post-processing models 213, record processing models 214, matching models 215, retrieval models 216, and/or any other model. The models can include architecture for machine learning approaches, classical or traditional approaches, and/or be otherwise configured. The models can include neural networks (e.g., CNN; DNN; CAN; LSTM; RNN such as LSTM, GRU, etc.; FNN; encoders; decoders; deep learning models; transformers; etc.) configured with image encoder architecture and large language model (LLM) architecture, regression, decision tree, LSA, clustering, association rules, dimensionality reduction, ensemble methods, optimization methods, classification, rules, heuristics, equations (e.g., weighted equations, etc.), selection (e.g., from a library), regularization methods (e.g., ridge regression), Bayesian methods (e.g., Naiive Bayes, Markov), instance-based methods (e.g., nearest neighbor), kernel methods, support vectors (e.g., SVM, SVC, etc.), statistical methods (e.g., probability), comparison methods (e.g., ranking, similarity, matching, distance metrics, thresholds, etc.), deterministics, genetic programs, and/or any other suitable model. The models can include (e.g., be constructed using): a set of input layers (e.g., encoders), output layers (e.g., decoders such as beam search decoders), and/or hidden layers (e.g., connected in series, such as in a feed forward network; connected with a feedback loop between the output and the input, such as in a recurrent neural network; etc.; wherein the layer weights and/or connections can be learned through training); a set of connected convolution layers (e.g., in a CNN); attention mechanisms (e.g., sequence-to-sequence architecture; a set of attention layers and/or self-attention layers; etc.); and/or have any other suitable architecture.

Models can be trained (e.g., pre-trained, retrained, tuned, fine-tuned, etc.), learned, fit, predetermined, untrained, and/or can be otherwise determined. The models can be trained or learned using: supervised learning, unsupervised learning, self-supervised learning, semi-supervised learning (e.g., positive-unlabeled learning), reinforcement learning, transfer learning, Bayesian optimization, fitting, interpolation and/or approximation, backpropagation, and/or otherwise generated. Models can be trained using feedback from inputs/queries provided by a working radiologist at user interface 235, retrieved and rendered information at the radiology workstation, followed by further inputs/queries provided by the working radiologist. The further inputs/queries provided by the working radiologist can be used to refine the models described, where such inputs can indicate relevancy of the rendered information, such that improved information retrieval and rendering can be performed.

Additionally or alternatively in other examples, models can be trained based on historical radiology reports (e.g., annotated radiology reports), manually generated radiology reports, synthesized radiology reports, labeled data, unlabeled data, positive training sets, negative training sets, and/or any other suitable set of data. Models can optionally be trained and/or undergo post-processing using: an additional model (e.g., a first model is used to teach a second model), autonomous agents (e.g., while models interact with each other), and/or any other model interactions.

The set of models 210 can include multimodal models that can receive inputs and/or queries (e.g., text-based queries, dictation-based queries, text-based inputs, dictation-based inputs, input device inputs, image data inputs, and/or other inputs), and return radiology outputs that have been actively transformed in a manner that provides key information to the querying entity/input-providing entity, in a format that increases working efficiency. In variations and examples described, the trained multimodal models can be used to process inputs, retrieve information, and render information rapidly, with respect to durations of time from input to rendering. In examples, durations of time can be less than 3 seconds, less than 2 seconds, less than 1 second, less than 0.5 seconds, less than 0.25 seconds, less than 0.1 seconds, less than 0.005 seconds, or less. Furthermore, rendered information can be dynamically updated with unprecedented performance, as the querying entity/input-providing entity continues to work and provide further inputs, where dynamically updating rendered information can include removing or moving positions of prior provided information, and placing updated information that has been retrieved, in position at the user interface (e.g., in a manner that highlights relevant information to improve working efficiency).

The set of models can thus include image models (e.g., vision models, trained transformers, deep learning transformers, machine learning transformers, neural networks, recurrent neural networks, etc.), wherein the set of image models are collectively configured to translate image-based information into a representation (e.g., embeddings) that are processed with text embeddings by a language-based model (e.g., large language model (LLM), natural language model, etc.), wherein this translation, is used to process multimodal inputs and provide multimodal outputs. Additional aspects of multimodal modals are described in more detail below.

The computing system 220 can include one or more: CPUs, GPUs, custom FPGA/ASICS, processors, microprocessors, servers, cloud computing, storage; memory; and/or any other suitable components. The computing system can be local (e.g., as a local computing system 121), remote (e.g., as a remote computing system 122), distributed, or otherwise arranged relative to any other system or module.

The system 200 can include and/or interface with a set of databases 230 (e.g., EHR, EMR, RIS, CIS, PACS, etc.). Additionally or alternatively, the system can include and/or interface with: a reporting platform 140; a Picture Archiving and Communication System (PACS) and/or alternative image viewing and image storage platform; a speech recognition platform; a radiology worklist; a Radiology Information System (RIS); an electronic medical record (EMR) database; an electronic health record (EHR) database; a Clinical Information System (CIS) platform; a Health Information System (HIS) platform; a Laboratory Information System (LIS) platform; vendor-neutral archive (VNA) components; ontologies (e.g., radiological or other clinical ontology database); and/or any other database, storage, server, and/or software tools.

Figure 3:
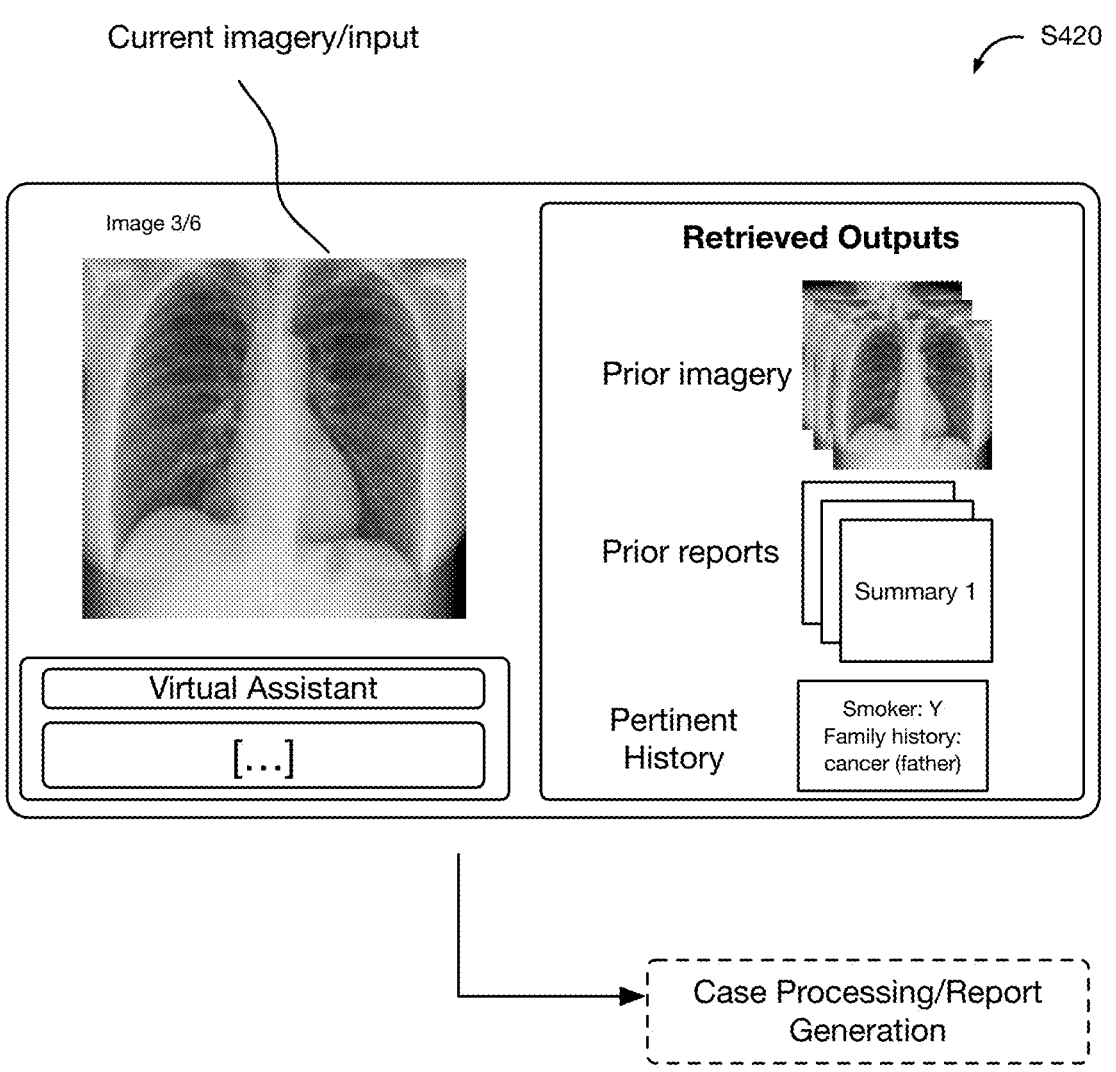
FIG. 3 is an illustrative representation of a variant of a dashboard.
Figure 4A:
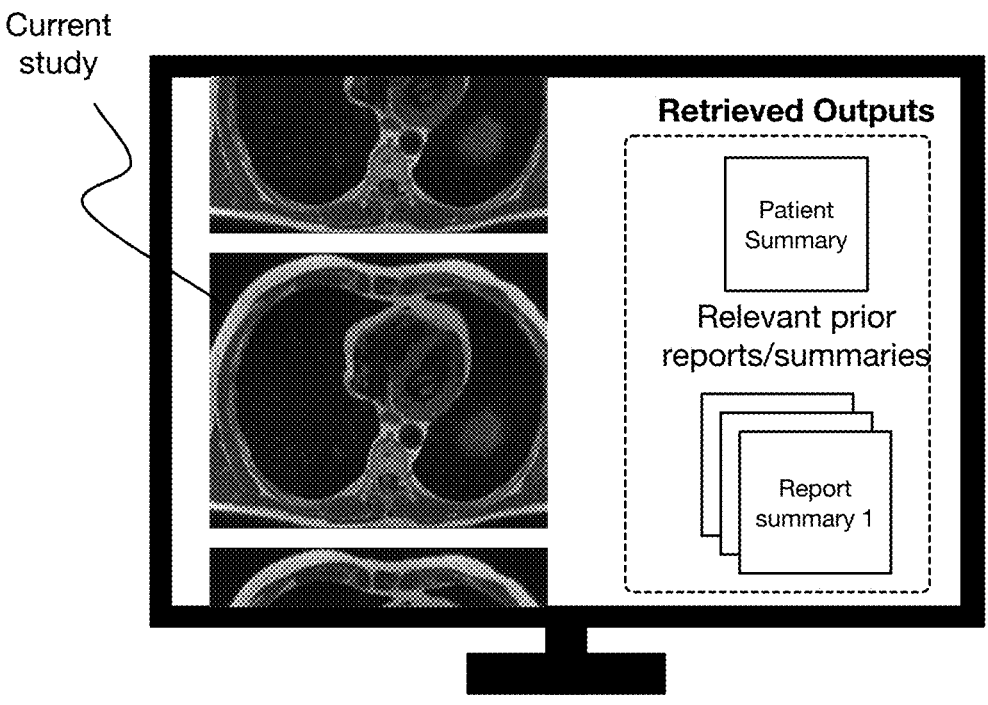
FIGS. 4A and 4B are illustrative representations of variants of a dashboard.
Figure 4B:
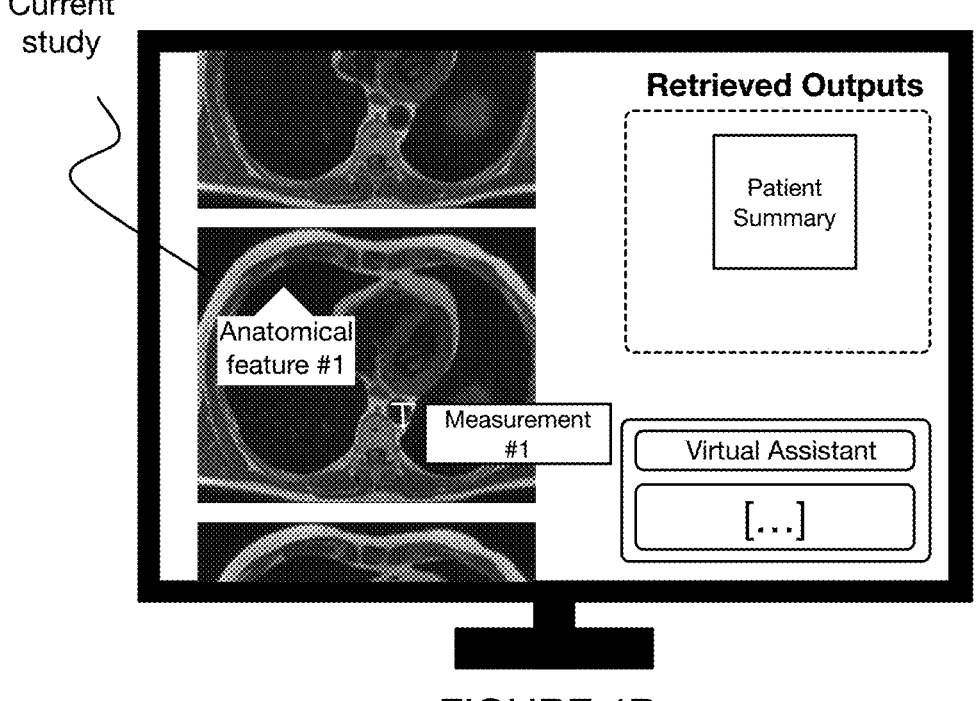

In a specific example, the system includes a reporting platform 240 (including a speech recognition platform and a user interface), wherein the reporting platform receives inputs and/or user actions from a radiologist, and displays a generated radiology report (e.g., determined using one or more models). In variants, the reporting platform 240 can include an input interface 241 (e.g., microphone, text box, etc.), which can function to receive input from a user (e.g., unstructured input), a speech transcription platform 242, and/or any other suitable components. The input interface can be rendered at a display of a user device (e.g., as shown in FIGS. 3, 4A, and 4B), part of an audio input device (e.g., the user device, microphone associated with speech-to-text software, etc.), include any combination of devices, and/or include any other device(s). In examples, the user device can include: a computer (e.g. a radiologist workstation computer), a headset (e.g., a virtual reality (VR) headset, an augmented reality (AR) headset, etc.), a mobile device (e.g., smartphone), and/or any other suitable device. Components of a user device can include a display subsystem (e.g., monitor, screen, projected image, etc.), an input subsystem (e.g., keys, touchscreen, microphone, etc.), one or more sensors (e.g., inertial measurement units, accelerometers, gyroscope, cameras, etc.), a processing subsystem, and/or any other suitable subsystem. Optionally, the system can include and/or interface with a software development kit, wherein customers and/or third parties can build additional features (e.g., further tools, features, functionality, analytics, historical report search, etc.) on top of the system (e.g., the reporting platform). The system 200 can include and/or interface with an optional reporting platform.

The reporting platform 240 can optionally include a virtual assistant 243 (e.g., chat bot, voice-based assistant, etc.), which can function to provide information to and/or receive information from a user. In variants, the virtual assistant can receive input from a user and determine an appropriate response. In examples, the virtual assistant can respond by: answering a user question, directing the user to information (e.g., contained within the report, linked to outside of the report, etc.), update an error within the generated report, and/or otherwise function. Additionally or alternatively, the virtual assistant 243 can determine a set of information to surface to and/or solicit from a user. In examples, the virtual assistant can surface information (e.g., via a notification) to a user, such as: an indication that an error has been corrected, a section of a report that requires further review, contact information of another medical professional (e.g., on the patient's care team, a specialist, a clinical trial coordinator, etc.) and/or any other entity (e.g., patient emergency contact information), and/or any other suitable information. In further examples, the virtual assistant can prompt a user to provide an input (e.g., as a response to information surfaced to the user), which can include a direct input to the report (e.g., fill out an incomplete section of a report), an input required for one or more models to run (e.g., to fill out an incomplete section of a report, to perform an error correction, etc.), a selection (e.g., a positive or a negative selection, a selection from a plurality of options, etc.) of one or more model outputs (e.g., a verification/rejection of an error correction performed by the system, a dropdown menu selection, etc.), and/or any other suitable input. Additionally or alternatively to a reporting platform, the system (e.g., the set of trained models) can integrate directly with one or more external systems (e.g., RIS, PACS, HER, etc.), wherein the system can output a radiology report with minimal or no input from a radiologist.

The system 200 can additionally include and/or interface with any other suitable components.

However, the system can be otherwise configured.

4. METHOD

As shown in FIG. 1A, a method 100 for displaying information at a radiologist dashboard can include: receiving a set of inputs associated with a patient S100, retrieving a set of records associated with the patient S200, processing the set of records S300, determining and displaying a set of relevant information S400, optionally receiving a set of radiologist inputs S500, optionally updating the displayed set of relevant information S600, and/or any other suitable steps.

A variation of the method 100 can include additional steps, where, as shown in FIG. 1B, a method can include: at a panel of a display of a platform for radiology report generation, dynamically rendering relevant radiology outputs of a set of candidate radiology outputs, to a radiologist in response to receiving a set of inputs from the radiologist S401, wherein dynamically rendering relevant radiology outputs includes: at a computing system of the platform, receiving the set of inputs from the radiologist, the set of inputs associated with a session with a patient, and the set of inputs received during a time window as the radiologist is preparing a report using the platform S501; retrieving a set of candidate radiology outputs upon processing the set of inputs with the multimodal model, during the time window S201; dynamically rendering relevant radiology outputs of the set of candidate radiology outputs at the panel of a display, wherein dynamically rendering comprises adjusting display of relevant radiology outputs at the panel during the time window, as the radiologist provides the set of inputs during the time window S601.

The methods 100 for dynamic retrieval and rendering of radiology information is preferably performed during and integrated within a traditional radiology workflow. As such, the processes involved in the method 100 and any associated system can include and/or be configured to interface with the workflow, software, associated hardware, protocols, or other components of any or all of the following: a Picture Archiving and Communication System (PACS) and/or alternative image viewing and image storage platform, a voice and/or speech recognition platform, a Radiology Information System (RIS) and/or alternative patient tracking platform, an electronic medical record (EMR) database, an electronic health record (EHR) database, a Clinical Information System (CIS) platform and/or alternative management software, a Laboratory Information System (LIS) platform; a radiology worklist; a smart worklist; one or more vendor-neutral archive (VNA) components; ontologies (e.g., radiological or other clinical ontology database) and/or any other clinical and administrative health data standards (e.g., HL 7, etc.); and/or any other suitable components.

In relation to dynamic retrieval and rendering of information, methods described using systems described can involve processing inputs with trained multimodal model; s structured to retrieve information, and render information rapidly, with respect to durations of time from input to rendering. In examples, durations of time can be less than 3 seconds, less than 2 seconds, less than 1 second, less than 0.5 seconds, less than 0.25 seconds, less than 0.1 seconds, less than 0.005 seconds, or less. Furthermore, rendered information can be dynamically updated with unprecedented performance, as the querying entity/input-providing entity continues to work and provide further inputs, where dynamically updating rendered information can include removing or moving positions of prior provided information, and placing updated information that has been retrieved, in position at the user interface (e.g., in a manner that highlights relevant information to improve working efficiency).

In relation to dynamic retrieval and rendering of relevant information, methods described using systems described can be performed in a manner that significantly reduces workload and improves efficiency in relation to worklist processing and report generation. The invention(s) and models described can contribute to computing system and processing enhancements, and in variations, can contribute to: 30 minutes saved (e.g., per clinical shift, per caretaking shift, per radiologist shift), thus providing ~6% improved speed in relation to standard systems; 35 minutes saved (e.g., per clinical shift, per caretaking shift, per radiologist shift), thus providing ~7% improved speed in relation to standard systems; 40 minutes saved (e.g., per clinical shift, per caretaking shift, per radiologist shift), thus providing ~8% improved speed in relation to standard systems; 45 minutes saved (e.g., per clinical shift, per caretaking shift, per radiologist shift), thus providing ~9% improved speed in relation to standard systems; 50 minutes saved (e.g., per clinical shift, per caretaking shift, per radiologist shift), thus providing ~10% improved speed in relation to standard systems; 55 minutes saved (e.g., per clinical shift, per caretaking shift, per radiologist shift), thus providing ~11% improved speed in relation to standard systems; 60 minutes saved (e.g., per clinical shift, per caretaking shift, per radiologist shift), thus providing ~12% improved speed in relation to standard systems; 65 minutes saved (e.g., per clinical shift, per caretaking shift, per radiologist shift), thus providing ~13% improved speed in relation to standard systems; 70 minutes saved (e.g., per clinical shift, per caretaking shift, per radiologist shift), thus providing ~14% improved speed in relation to standard systems; 75 minutes saved (e.g., per clinical shift, per caretaking shift, per radiologist shift), thus providing ~15% improved speed in relation to standard systems; 80 minutes saved (e.g., per clinical shift, per caretaking shift, per radiologist shift), thus providing ~16% improved speed in relation to standard systems; or greater speed performance.

In relation to dynamic and retrieval of relevant information, methods described using systems described can be performed in a manner that significantly reduces workload and improves efficiency in relation to worklist processing, dictation, and report generation. In examples, the methods described can contribute to: dictation of 20% fewer words by clinicians/radiologists (e.g., in order to generate a report from a clinical session), dictation of 22% fewer words by clinicians/radiologists (e.g., in order to generate a report from a clinical session), dictation of 24% fewer words by clinicians/radiologists (e.g., in order to generate a report from a clinical session), dictation of 26% fewer words by clinicians/radiologists (e.g., in order to generate a report from a clinical session), dictation of 28% fewer words by clinicians/radiologists (e.g., in order to generate a report from a clinical session), dictation of 30% fewer words by clinicians/radiologists (e.g., in order to generate a report from a clinical session), dictation of 32% fewer words by clinicians/radiologists (e.g., in order to generate a report from a clinical session), dictation of 34% fewer words by clinicians/radiologists (e.g., in order to generate a report from a clinical session), dictation of 36% fewer words by clinicians/radiologists (e.g., in order to generate a report from a clinical session), dictation of 38% fewer words by clinicians/radiologists (e.g., in order to generate a report from a clinical session), dictation of 40% fewer words by clinicians/radiologists (e.g., in order to generate a report from a clinical session), dictation of 42% fewer words by clinicians/radiologists (e.g., in order to generate a report from a clinical session), dictation of 44% fewer words by clinicians/radiologists (e.g., in order to generate a report from a clinical session), dictation of 46% fewer words by clinicians/radiologists (e.g., in order to generate a report from a clinical session), dictation of 48% fewer words by clinicians/radiologists (e.g., in order to generate a report from a clinical session), dictation of 50% fewer words by clinicians/radiologists (e.g., in order to generate a report from a clinical session), or a lower percentage of words dictated by clinicians/radiologists (e.g., in order to generate a report from a clinical session). Dictation reduction performance can be determined, with comparisons to workflows that do not involve use of the methods and systems described.

The method(s) described can be executed using embodiments, variations, and examples of system aspects described above; however, the method(s) can additionally or alternatively be executed using other system components. However, the method can be otherwise performed.

4.1 Receiving a Set of Inputs Associated with a Patient

Receiving a set of inputs associated with a patient S100 can function to prompt the subsequent processes of the method 100, and/or otherwise function. In relation to method steps S401 and S501 shown in FIG. 1B, receiving the set of inputs in Step S100 can trigger dynamic rendering of relevant radiology outputs of a set of candidate radiology outputs, to a radiologist, as the radiologist is performing tasks (e.g., reviewing reports, generating reports, reviewing findings, etc.), where, retrieval and rendering are performed in real-time as the radiologist is working, without interruption of work.

Preferably the set of inputs include data related to a case currently being reviewed by a user of the system (e.g., a radiologist), related to a case in a review queue for the user, related to a report being generated by a user of the system, or other suitable input.

In variants, the inputs can include any or all of: a set of one or more images (equivalently referred to herein as "imaging exams", and "scans"), a series, and/or a study from an imaging modality (e.g., radiography/x-ray, computed tomography (CT), magnetic resonance imaging (MRI), ultrasound, positron emission tomography (PET)/CT, other forms of nuclear medicine, mammography, digital breast tomosynthesis, PET/MRI, etc.); images from one or more procedures (e.g., procedures involving fluoroscopy, molecular imaging, mammography, etc.), and/or any other suitable information. The inputs can additionally or alternatively include any or all of: video data (e.g., kinetics action data, video data of blood vessels, etc.), patient information (e.g., patient metadata, demographic information, etc.); patient condition information (e.g., predicted medical condition, previous medical condition, patient history, etc.); and/or any other suitable information.

Additionally or alternatively, the set of inputs associated with Steps S100, S401, and S501 can include querying inputs associated with various tasks. Such inputs can be provided to a virtual assistant (e.g., chatbot) component of embodiments of the user interface described in Section 3 above. In variations, inputs can be associated with various types of tasks (e.g., classification, zero-shot classification, data-efficient classification, search, semantic search, question answering, visual question answering, quality assurance, report quality assurance, etc.) involved for report generation or other radiologist tasks. Queries can be submitted as inputs using text, dictation, and/or other formats.

Figure 5A:
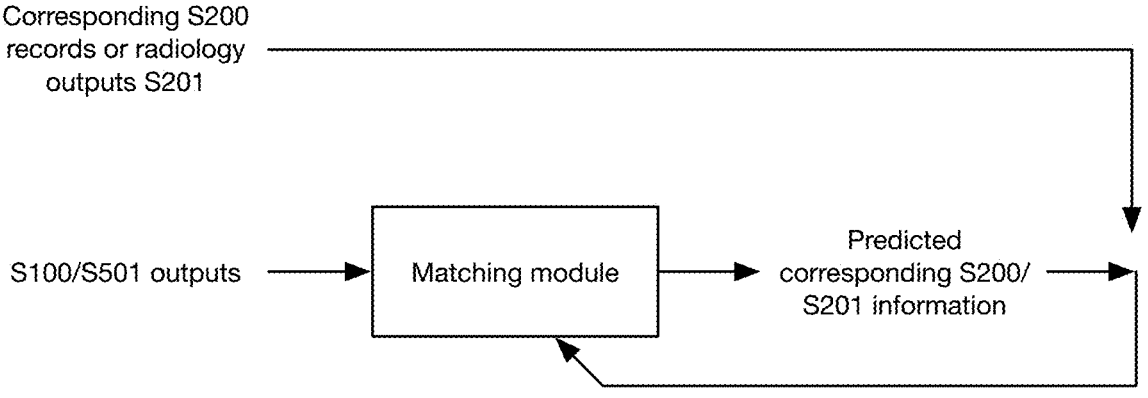
FIGS. 5A and 5B are schematic representations of variants of training and inference of a matching module, respectively.
Figure 5B:
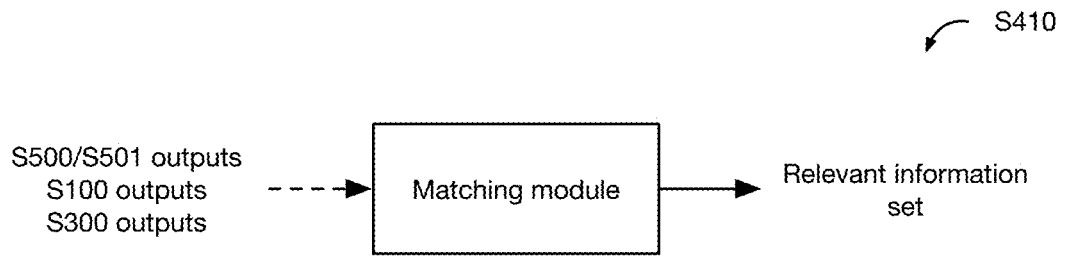

The set of inputs (e.g., instances, series, studies, etc.) can additionally or alternatively be received from an imaging modality (e.g., CT scanner, MRI scanner, etc.), such as from a RIS associated with the imaging modality (e.g., as shown in FIG. 4), a PACS associated with the imaging modality (e.g., as shown in FIG. 5), a combined RIS/PACS associated with the imaging modality, and/or any other suitable source. Additionally or alternatively, inputs (e.g., patient information, health records, etc.) can be received through an alternative server or database (e.g., local server at healthcare facility, remote server, cloud-based storage, etc.), an EMR database, an EHR database, or any other suitable software or storage.

Additionally or alternatively, the set of inputs can be received from a virtual assistant (e.g., chatbot) component of a user interface of a radiologist workstation. In one example, the set of inputs can include a search string/query (e.g., multi-word text) associated with an indication, and retrieval of a set of records or other information in Step S200 can involve retrieving historical records (e.g., historical clinical reports) capturing details related to the indication to provide context for the current case that the radiologist is working on. Inputs can relate to pathologies (e.g., a pathology), and Steps S200 and S201 can include processing the input with the trained multimodal model, for retrieval, processing, and display of historical records, images, and/or other radiology outputs related to the pathology(ies). Steps S100/S500/S501 can further include inputs that prompt retrieval of reports or other radiology outputs pertaining to differential diagnoses for the patient, using multimodal model architecture, in subsequent steps.

For instance, a radiologist or other clinical entity can provide, to the virtual assistant, an input of "cancer polyp", and retrieval in Steps S200 and S201 can include processing the input with the trained multimodal model, for retrieval, processing, and display of historical records, images, and/or other radiology outputs related to any cancer polyps of the patient, oncology panel results, and/or other related information.

In another example, the set of inputs can include an input provided through a dictation (e.g., spoken) query that is processed with the multimodal model. For instance, a radiologist or other clinical entity can ask the virtual assistant "does this patient still have an appendix", and retrieval in Steps S200 and S201 can include processing the input with the trained multimodal model, for retrieval, processing, and display of historical records, images, and/or other radiology outputs related to the appendix of the patient.

The set of inputs can be associated with a session with a patient (e.g., an imaging session, a follow-up session, an initial visit, a visit, etc.).

In relation to step S501 shown in FIG. 1B, the set of inputs is received during a time window as the radiologist is performing tasks (e.g., preparing a report, reviewing findings, performing analytical work, etc.). In variations, the time window can have a duration of less than 1 hour, less than 50 minutes, less than 40 minutes, less than 30 minutes, less than 20 minutes, less than 10 minutes, less than 5 minutes, less than 4 minutes, less than 3 minutes, less than 2 minutes, less than 1 minute, or a lower duration of time. As such, in variations, receiving the input and dynamically rendering key/relevant information can be performed in a manner that is not possible for a human to perform. The time window can be a continuous time window, or can be a time window that is divided into phases (e.g., phases associated with specific tasks, phases associated with shifts, etc.).

In variants, the method can include pre-processing the set of inputs. In examples, pre-processing the set of inputs can include any of the steps described in U.S. patent application Ser. No. 16/688,623, filed 19 Nov. 2019, which is incorporated herein in its entirety by this reference.

However receiving a set of inputs associated with a patient S100 can be otherwise performed.

4.2 Retrieving Records and Radiology Outputs Associated with the Patient S200.

Retrieving a set of records associated with the patient S200 can function to retrieve medical history and/or any other suitable records for the patient, which can be used as input for subsequent steps of the method. Relatedly, Step S201 recites retrieving a set of candidate radiology outputs upon processing the set of inputs with a multimodal model, during the time window, which functions to rapidly retrieve the most relevant radiology outputs associated with a task being performed by the radiologist/user, in order to enhance their performance. Steps S200 and S201 can function to save time for a radiologist who would otherwise have to manually retrieve patient records, and/or otherwise function, which would significantly increase workflow processing times and could involve retrieval of non-relevant information. Use of multimodal models in relation to Steps S200 and S201 can thus function to use trained models to retrieve information with a degree of rapidness and a degree of relevancy that is unprecedented, and that is substantially higher-performing than human/manual retrieval of such information.

S200 is generally performed after S100 (e.g., patient records are retrieved for a patient each time a new study is received) and before S300-S600, but can additionally or alternatively be performed at any other times (e.g., prior to S100, responsive to S500, after S300, interspersed or performed contemporaneously with other steps, etc.). For instance, in relation to methods shown in FIG. 1B, retrieving candidate radiology outputs can be performed after processing the set of inputs described.

S200 generally includes retrieving a set of one or more digital files (e.g., via an application programming interface (API), a REST API, an FHIR-compliant API, etc.) from an external platform, but can additionally or alternatively include retrieving digital files stored within the system (e.g., a database, internal platform, etc.). The external platform can include a server of a healthcare facility (e.g., local, remote, etc.), a health information technology platform (e.g., RIS, PACS, EMR services, an EHR services, etc.), In variants, a set of records associated with the patient can include any or all of: clinical contexts (e.g., CT scan parameter information, MRI parameter information, X-ray parameter information, use of contrast information, etc.); test panel results (e.g., blood urea nitrogen results, creatinine test results, glomerular filtration rate test results, blood pressure test results, cardiovascular stress test results, blood test results, comprehensive metabolic panel results, basic metabolic panel test results, allergen panel test results, respiratory panel test results; bone panel test results, inflammatory panel test results, liver panel test results, infection/pathogen panel test results; sexual health panel test results, etc.), such that the set of candidate radiology outputs includes a test panel result providing a clinical context associated with at least one of the set of inputs; patient demographics data (e.g., age, race, gender, etc.); patient administrative data; medical information (e.g., symptoms, diagnosis, weight, medicines, treatments, allergies, smoker status, surgical history, etc.); past images (e.g., scans) of the patient and/or associated reports from which the radiologist can review any missed information, findings (e.g., nodule findings), measurements, etc.; EHR; EMR; laboratory test results (e.g., pathology, referred to equivalently herein as "labs"); prior clinical reports; family history (e.g., disease, smoking, etc.); prior observations; prior diagnostics; notes and/or other records from past medical visits (e.g., routine care, specialist care, urgent care, physical therapy, psychiatry, neurology, cardiology, orthopedics, etc.); behavioral history; prior report summaries (e.g., indicating how conditions, such as masses, have evolved over time in relation to morphological features, cell type distributions, tissue composition, tissue density, etc.); and/or any other information.

In variants, S200 can optionally include consolidating information from a plurality of external platforms (e.g., Epic, Cerner, PACS, RIS, etc. etc.) by identifying a set of (e.g., one, multiple, etc.) external platforms storing records for the patient (e.g., all platforms storing medical records for the patient, a subset thereof, all in a particular country, etc.), and retrieving records from the identified set of external platforms. Consolidating information can be particularly beneficial when a patient has health records stored across a plurality of platforms by reducing or eliminating a need for a radiologist to interact with platform individually. S200 can optionally include consolidating information stored at external platforms with information stored at an internal platform of the system.

In variants, S200 can optionally include pre-filtering and/or pre-processing patient records to determine which records to retrieve and/or process further (e.g., in S300). Optionally, only records that are possibly relevant to the current case are retrieved.

S200 can optionally be performed by a retrieval module, which can optionally include a set of one or more rules. Additionally or alternatively, the retrieval module can include one or more trained models (e.g., as described above), and/or any other tools or combination of tools.

In a first variation, the retrieval module (e.g., retrieval module 216 shown in FIG. 2A) can retrieve all medical records for the patient (e.g., for subsequent processing in S300).

In a second variation, the set of rules can define a subset of medical records (e.g., by type) to retrieve for all case types (e.g., patient age, gender, surgical history, history of hospitalizations, family disease history, others risk factors, and/or any other suitable information). S200 and relatedly S201 can include retrieving (e.g., with the retrieval module) all records of the specified type, as candidate radiology outputs for subsequent processing and rendering at a radiology workstation.

In a third variation, S200 and relatedly, S201, can include retrieving (e.g., with the retrieval module) all records of the specified type based on the associated rules. S200 can be performed programmatically, and/or with models. The set of rules can define a subset of medical records (e.g., by type) to retrieve depending on information received at S100, which can optionally function to only retrieve records that are potentially relevant to the case. In examples, the type or types of medical records and/or radiology outputs to retrieve (e.g., as candidate radiology outputs) can be defined (e.g., filtered) by on one or more of: a date range, case type, scan type, physician notes received with the scan, patient risk factors (e.g., age, smoker status, etc.), patient history (e.g., surgical, mental health, etc.), administrative information (e.g., reason for visit), and/or any other suitable information. In a first specific example, certain medical records can always be retrieved for a particular case type (e.g., for a pulmonary scan, always retrieve smoking status; for scans related to cancer, always retrieve family history; etc.). In a second specific example, if the inputs of S100 are associated with a particular body region (e.g., include a scan of the body region), S200 and S201 can include retrieving all existing images and/or other records of the same body region and/or a related body region. In a third specific example, if an input (e.g., the inputs of S100, a radiologist input at S500) includes an indication of an associated pathology and/or treatment option, S200 and S201 can include retrieving any patient records pertaining to the pathology and/or treatment option, and/or pertaining to a related pathology and/or treatment option.

In a third variation, S200 and S201 can include retrieving records requested by radiologist (e.g., at the dashboard).

However retrieving a set of records associated with the patient S200 can be otherwise performed.

For instance, in some variations, the set of inputs received in Steps S100 and S501 can be processed with a trained multimodal model, where the trained multimodal model is structured to process the set of inputs and return candidate radiology outputs for rendering, based upon a set of criteria. In examples, the trained multimodal model can include image encoder components configured to generate image embeddings from image data inputs, as well as large language model (LLM) components. The trained multimodal model can include a set of image encoders, where each of the set of image encoders is trained using data from a specific imaging modality. As such, each image encoder of the image encoder component can be structured and trained to process input images from a corresponding imaging modality (e.g., x-ray image vision encoder, computed tomography image vision encoder, magnetic resonance imaging image vision encoder, nuclear image vision encoder, optical coherence tomography image vision encoder, other image vision encoder, etc.); however, the set of image encoders can be otherwise configured.

In a specific example, the multimodal model comprises a language-aligned image encoder integrated, by way of an adapter, onto an LLM. In examples, the LLM can include a version of the Pathways Language Model (e.g., PaLM, PaLM2, etc.). Variations of the LLM can include a version of a Language Model for Dialogue Applications (LaMDA), a Gemini model (e.g., a decoder-only transformer), a GPT model, a Llama model, a GLM model, a Claude model, a Reka Flash model, a Qwen model, a Grok model, a Molmo model, a Jamba model, a DeepSeek Coder model, an Athene model, a Phi-3 model, a Command-R-Plus model, an InternLM model, a Yi-Large model, a Mixtral of Experts model, a Gemma model, a Nemotron model, and/or another suitable model.

The multimodal model can thus receive a diverse set of inputs (e.g., dictation data, text data, images, audio, etc.) and return relevant outputs in relation to various queries/inputs, where the outputs are then processed (e.g., according to Step S300) and rendered for presentation to the radiologist or other clinical entity at a workstation. The multimodal model can have a context length of: up to 3,000,000 tokens, up to 2,000,000 tokens, up to 1,000,000 tokens, up to 500,000 tokens, up to 100,000 tokens, up to 90,000 tokens, up to 80,000 tokens, up to 70,000 tokens, up to 60,000 tokens, up to 50,000 tokens, up to 40,000 tokens, up to 35,000 tokens, up to 33,000 tokens, up to 30,000 tokens, up to 25,000 tokens, or another suitable number of tokens. Each context window can contain multiple forms of input, and different modes can be interleaved without requirement to be presented in a fixed order, allowing for a multimodal conversation. Input images can be of different resolutions. The multimodal model can have sparse mixture-of-experts architecture or other architecture.

Aspects of model training are further described in Section 4.7 below.

4.3 Processing the Set of Records

Processing the set of records S300 can function to extract key information from patient records and candidate radiology outputs (e.g., the set of records retrieved at S200, the radiologist inputs received at S500, the set of inputs received at S100, candidate radiology outputs of S201), and/or otherwise function. The processed records and/or candidate radiology outputs (e.g., information extracted from the records) can be used as input to the matching module in S400 (e.g., matching module 215 shown in FIG. 2A). S300 is preferably performed after S200/S201, but can additionally or alternatively be performed at any other suitable time. Additionally or alternatively, S300 can include processing the set of relevant information determined by the matching module in S400.

S300 is preferably performed by a record processing module (e.g., record processing module 214 shown in FIG. 2A), which can include one or more record processing models and/or algorithms (e.g., text extraction algorithms and/or software, rule-based algorithms, etc.). Additionally or alternatively, S300 can be performed by record processing platform (e.g., radiology platform, automated image processing platform, etc.). In variants, the record processing module can output one or more of: values, normalized values and/or codes, key value pairs and/or any other similar data structure (e.g., type of lab result and the numeric value), summaries (e.g., of text-based documents), findings (e.g., from an annotated or un-annotated scan), dates, outcomes, recommendations, potential diagnoses, and/or any other suitable information.

In variants, S300 can optionally be performed for (e.g., responsive to) the set of inputs received from the radiologist at S500 and/or S501. In specific examples, S300 is repeated each time a radiologist makes a new finding (e.g., by annotating a radiology image, by filling in a report, by dictating the finding, etc.), in response to receiving a radiologist question (e.g., verbal, written, etc.) and/or button press, and/or otherwise performed.

S300 can optionally include standardizing and/or transforming a data file type of one or more patient records. In examples, S300 can include receiving the data file in a first format provided by a first platform (e.g., JSON file, etc.) and altering the data file into a second format (e.g., altering the file format, altering the data structure, etc.). Transforming a data file can optionally function to modify the file for the purposes of displaying the file (e.g., at S400/S600/S401/S601).

S300 can optionally include normalizing one or more radiology outputs, records, record values. In examples, S300 can optionally include exam code normalization, including mapping a received phrase to a standardized code. Standardized codes can include: Logical Observation Identifiers Names and Codes (LOINC) code, Systemized Nomenclature of Medicine-Clinical Terms (SNOMED CT) code, OPCS, a set of numerical values (e.g., encoding), and/or any other medical ontologies and/or set of values. In a specific example, a record value can include one of a plurality of phrases (e.g., X-ray hand, XR upper extremity, hand x-ray, hand CR, etc.) that all share a common meaning, and S300 can include determining a standardized code that the value maps to (e.g., the corresponding LOINC code).

In an example, the model(s) used for processing can include one or more language models (e.g., large language models [LLMs]) configured for natural language processing (NLP). In a specific example, models can include: one or more transformers and/or transformer systems (e.g., Bidirectional Encoder Representations from Transformers [BERT], Generative Pre-Trained Transformer [GPT], etc.); a transformer with any suitable number and/or arrangement of encoders and decoders (e.g., arranged in a sequential and/or parallel arrangement); and/or any other suitable transformers, transformer-based models, or models. As described, the models can be multimodal, with the ability to perform different tasks described.

In a first variation, S300 can include processing records (e.g., text-based data, audio, etc.) using one or more multimodal models, language models (e.g., LLMs, transformer-based models, NNs, ML models, etc.) and/or any other natural language processing techniques. In examples, processing records can include producing summaries of longer texts and/or audio recordings, classification of semantic meaning, mappings between record values and codes, and/or other suitable outputs.

In a second variation, S300 can include processing records using one or more algorithms and/or models (e.g., rule-based models). In examples, processing records can include extracting specific values (e.g., numeric values, diagnoses, treatment history, etc.) from a record (e.g., medical chart, report, timeline, file, annotated image, etc.). As such, candidate radiology outputs can include a set of annotated images from historical radiology reports and/or other suitable information.

In a third variation, S300 can include automatically reviewing an image (e.g., scan, lab, etc.). Automated image review can be performed by the system and/or an external platform (e.g., an automated image review software). In a specific example, a record processing model can be configured to automatically determine findings in one or more images, for example, using any of the techniques described in U.S. patent application Ser. No. 16/688,623, filed 19 Nov. 2019, which is incorporated herein in its entirety by this reference. An annotation can include an indicator for a radiologist to view (e.g., on a PACS, at a PACS viewer, at a radiologist workstation, etc.) or otherwise perceive each annotation corresponding to one or more outputs as reflected in the labels. In some variations, the annotation is in the form of a hover box, which can be viewed, for instance, at or near a mouse cursor on a display (e.g., monitor at a radiologist workstation). The hover box can include any or all of: text (e.g., reciting a particular finding, reciting the value of a measurement, etc.), an image (e.g., a simplified symbol corresponding to a finding, a simplified symbol corresponding to an anatomic region, etc.), a link (e.g., to a relevant prior study, to a corresponding image in the same study, web link, etc.), or any other suitable information. Additionally or alternatively, annotations can include stationary boxes (e.g., text boxes); any number of location indicators, such as, but not limited to: arrows (e.g., pointing to a particular anatomy), lines (e.g., separating anatomical features), circles (e.g., encircling a region corresponding to an abnormal finding); images; and/or any other suitable indicator(s). In a specific example, for instance, a combination of hover boxes and arrows are used to locate and specify each rib in a scan of a patient's torso. The annotation location on the input is preferably chosen to clearly and quickly indicate the region of interest as well as to minimize crowding and/or blockage of important regions; additionally or alternatively, the annotation location can be chosen in any suitable way. In relation to S300, a feature of an annotation (e.g., color, size, duration for which it appears, etc.) can be determined and/or adjusted based on any or all of: the severity of a finding, the importance of a finding, the novelty of a finding, the value of a measurement (e.g., to indicate that a value is within a normal range, to indicate that a value is outside of a normal range, etc.), its relationship to another annotation (e.g., to a comorbidity finding), or any other suitable parameter. Processing S300 can thus include adjusting annotations (e.g., removing annotations, adding new annotations from dynamically-retrieved radiology outputs in response to queries, etc.) live, during the time window, as the radiologist is working.

In examples, automatically determine findings can include determining a finding, flagging a finding input by a radiologist as potentially incorrect, flagging a change in a condition (e.g., abnormal growth, aneurism, etc.) over time (e.g., by comparing image or finding to a prior image or finding), and/or any other suitable actions. Optionally, the entire method can be automated, wherein S500 can be performed automatically by a record processing model.

S300 can optionally include training one or more record processing models. In examples this can include any of the training methods described herein, any standard training techniques, any of the techniques described in U.S. patent application Ser. No. 17/020,593, filed 14 Sep. 2020, which is incorporated herein in its entirety by this reference, and/or any other suitable training techniques. In a specific example, a secondary model (e.g., an LLM) can be trained to generate text to simulate a medical professional interacting with a radiology report (e.g., pose questions, flag missing information, flag inaccuracies, etc.), wherein the output of the secondary model can be used (e.g., as a training target, as an additional feature, etc.) to train, re-train, or refine the matching module.

In relation to radiology reports and images retrieved in S300, processing can include adjusting fields of view and/or other aspects of retrieved digital files, prior to rendering of such aspects in steps S400/S401/S600/S601. Processing can include automatic cropping (e.g., to provide a focused field of view for rendering), adjusting resolution (e.g., to enhance definition or sharpness of an aspect of retrieved information for rendering); automatically adjusting zoom (e.g., to provide a zoomed in or zoomed out field of view for rendering); automatically rotating features; automatically adjusting highlighting of specific features (e.g., anomalies, anatomical features, report text, etc.) of retrieved radiology outputs; moving positions of retrieved and rendered radiology outputs in response to cursor inputs, in coordination with S400/S401/S600/S601, and/or performing other adjustments.

However processing the set of records/radiology outputs S300 can be otherwise performed.

4.4 Determining and Displaying/Rendering a Set of Relevant Information.

Determining and displaying a set of relevant information S400 can function to determine a set of information from the patient records (e.g., the process patient records) that is relevant to display to the radiologist, determine how to display the set of relevant information, display the set of relevant information, and/or otherwise function. Relatedly, S401 and S601 can include dynamically rendering relevant radiology outputs of the set of candidate radiology outputs at the panel of a display, wherein dynamically rendering comprises adjusting display of relevant radiology outputs at the panel during the time window, as the radiologist provides the set of inputs during the time window S601.

Determining a set of relevant information S410 can include mapping the set of inputs associated with the patient received at S100/S501 to the set of records processed at S300, and/or to the set of records retrieved at S200/S601.

Determining a set of relevant information is preferably performed by a matching module (e.g., clinical guidance module, example shown in FIG. 5B, etc.), which can include one or more matching models (e.g., trained models such as transformer-based models, NNs, etc.; untrained models such as algorithms, rule-based models, etc.) of a multimodal model. In variants, inputs to the matching module and/or model can include any or all of: the radiologist inputs (e.g., as received at S500), the set of patient inputs (e.g., as received at S100/S501), the set of records (e.g., as determined at S300), and/or any other suitable input. In variants, outputs of the matching module and/or model can include a set of information retrieved from the patient's records (e.g., at S200/S201) and/or from a supplementary corpus of information (e.g., other patient records, medical database, etc.). The matching module can also include architecture for detecting and resolving contradictions in prior and current data, and to explain and resolve those contradictions for the radiologist as part of the relevant information being displayed. In one example, if a prior report notes that a prior appendectomy was performed and the medical history of the patient indicates question of appendectomy, but the model returns outputs indicating presence of an appendix in prior and/or current imaging studies, outputs generated using the matching module can be rendered, in order to explain and resolve the contradictions related to appendix presence.

Determining a set of relevant information can optionally include determining a relevancy metric (e.g., numerical, categorical, etc.) for a specific record, and categorizing the record as relevant when the relevancy metric exceeds a threshold. In examples, the threshold can be a predetermined value, a ranking within a set of records each determined potentially relevant, and/or otherwise determined. As such, candidate radiology outputs retrieved in Step S201 can be ranked accordingly.

In variants, determining the set of relevant information can include algorithmic and/or rule-based retrieval methods, machine learning methods (e.g., NNs, LLMs, transformers, etc.), combinations thereof, and/or any other suitable mapping methodologies, including multimodal model aspects described. In examples, the matching module can be trained (e.g., example shown in FIG. 5A) to map one or more sets of information received at S100/S501 to specific sets of information from the patient record at determined at S200/

S201 (e.g., based on scan type, diagnosis, pathology, patient history, etc.). Further aspects of training are provided in Section 4.7 below.

In a first variation, the matching module can be configured to retrieve any patient records (e.g., visits, labs, reports, etc.) corresponding to a pathology associated with the current case (e.g., as indicated in the inputs of S100, as indicated by the user, etc.). Retrieving patient records associated with the pathology can confer the benefit of reducing a likelihood that a radiologist recommends an unnecessary follow-up as method enables the radiologist to review all prior follow-ups.

In a second variation, the matching module can be configured to retrieve any patient records that could help narrow a differential diagnosis. The differential diagnosis report can be input by radiologist, determined by an automated model, inferred from the S100 inputs (i.e., the lab ordered can be associated with a set of potential outcomes), and/or otherwise determined. In an example, the matching module can be configured to retrieve lab results (e.g., biopsy, etc.) associated with a finding (e.g., a tumor) within a radiology image that indicate a classification of the finding (e.g., benign vs. malignant).

In a third variation, the matching module can be configured to detect missing data (e.g., in a report). In an example, the output of the matching module can be used (e.g., at S600) to guide the user fill in the missing information.

Displaying the set of relevant information S420 and/or rendering information in Steps S401/601 can be performed immediately upon determining the set of relevant information, or at a subsequent time point. Optionally, displaying the set of relevant information can be performed responsive to a trigger, which can include: an input received at S500/S501 (e.g., a position of a radiologist within a report, a request or command, an annotation, etc.), a time threshold, an urgency threshold, and/or any other suitable condition. Rendering information is preferably performed during the time window in which the radiologist is working (e.g., during a shift, during processing of a case), where time window aspects are described above.

Displaying the set of relevant information can be performed at a dashboard. The dashboard can optionally include one or more of: an image viewing interface, an image annotation interface, a document filling interface, a text display, a dictation tool, a virtual assistant (e.g., chatbot), and/or any other components. In examples, rendering is performed at a panel of a dashboard (e.g., a first panel of a dashboard) configured for display of retrieved information, while the radiologist or other clinical entity is providing inputs at another (e.g., second panel, third panel) of the dashboard S420 can include rendering all case information (e.g., patient demographics, reason for exam, imaging study done, type of study) at the dashboard (e.g., example shown in FIG. 3). S420 can optionally include displaying radiology images and/or records (e.g., those received at S100, prior records retrieved at S300, etc.) directly within the dashboard, and/or linking the user to an external platform.

S420 preferably includes displaying summaries of patient records including key information, but can additionally or alternatively include displaying retrieved patient records in their original format (e.g., an entire report). In examples, the dashboard can be configured to display summaries of each recent biopsy report in a set of tabs that the radiologist can click through, and enable the radiologist to click on a specific report to read it in its entirety. In variations, summarization of prior report(s) can be provided as a single summary of relevant key information that is tracked over time, as individual summaries of prior reports (e.g., with extracted key information for each report), and/or as summary of how a single particular finding has evolved over multiple prior reports (e.g., depending on which finding is currently being reviewed in images or dictated into the report).

S420 can include presenting information in a graphical or text-based format. In a first variant (e.g., example shown in FIG. 4A), S420 can include presenting information (e.g., text-based summaries) adjacent to one or more of the inputs received at S100. In a second variant, (e.g., example shown in FIG. 4B), S420 can include directly labeling one or more of the inputs (e.g., images) received at S100. In a specific set of examples, S420 can include indicating a patient's anatomical modifications and/or known anatomical abnormalities that could show up in images, including: removed/partially removed anatomy (e.g., gall bladder, appendix, kidney, etc.), replacement procedures (e.g., joint replacement), reconstructive surgeries, cosmetic surgeries, and/or any other modification. The dashboard can present a written description of the modifications/abnormalities adjacent to the image, or directly label the images for ease of viewing by the radiologist.

However determining and displaying a set of relevant information S400 can be otherwise performed.

4.5 Receiving a Set of Radiologist Inputs, for Updating Retrieval and Rendered Information The method can optionally include receiving a set of radiologist inputs S500, which can function to receive radiologist and/or other user input which can be used to update the displayed set of relevant information at the dashboard (e.g., in S600/S601). The radiologist inputs, once received, can be treated as patient records and processed at other steps of the method (e.g., at S300).

In examples, radiologist inputs can be explicitly provided by the user, implicitly interpreted by the system, and/or otherwise specified.

In a first variation, the set of radiologist inputs can include interactions with the radiologist and an imaging exam (e.g., the current imaging exam being examined by the radiologist, a prior imaging exam of the patient, etc.). In a specific example, a radiologist input can include an annotation added to the imaging exam by the radiologist.

In a second variation, the set of radiologist inputs can include interactions with the radiologist and a radiology report. In examples, radiologist inputs can include text from a radiologist filling out a report, audio from a radiologist dictating to a reporting platform, a position provided by the radiologist within a report (e.g., a cursor position, a scroll position, etc.), and/or any other input.

In a third variation, the set of radiologist inputs can include an active request received from the user (e.g., the radiologist). In specific examples, radiologist inputs can include a text-based command (e.g., a voice command or question, a typed command or question, etc.), an interaction with the dashboard (e.g., a GUI thereof) and/or computing system of the user (e.g., a button click, a keyboard press, a scroll, a click, a dragging of a graphical object, a selection within a GUI, etc.), and/or any other suitable command. In further specific examples, the radiologist can make a selection within a GUI of the dashboard that links them to further information.

Rendering relevant radiology outputs can include removing or replacing a previously-rendered radiology output from the panel in response to receiving the set of inputs.

However receiving a set of radiologist inputs S500 can be otherwise performed.

4.6 Dynamically Updating Displayed/Rendered Information

The method can optionally include updating the displayed set of relevant information S600/S601, which can function to change set of information displayed to the user (e.g., radiologist) based on one or more inputs.

Preferably, S600/S601 includes updating (e.g., dynamically updating) the displayed set of relevant information based on inputs received directly or indirectly from the user. However, S600/S601 can additionally or alternatively be performed based on inputs received from any other source (e.g., an additional input added to the patient record, a communication from an external user, etc.), based on predefined parameters (e.g., a time threshold being reached, a lack of an input, etc.), and/or any other suitable trigger. S600/S601 can optionally include triggering S400 to be repeated to determine new relevant information based on the input.

S600 can optionally include waiting for satisfaction of a trigger condition to display a set of information. In examples, the trigger condition can include a radiologist moving on to a new section of a report (e.g., as detected based on a location of the radiologist's cursor within the report) without mentioning a piece of information determined relevant (e.g., at S400/S401) by the system. In variants, S600/S601 can include maintaining a first checklist of information added to a radiology report by the user and a second checklist of information determined relevant to include within the radiology report by the system (e.g., at S400/S401), and displaying missed information (e.g., information within the second checklist not included in the first checklist).

In a first variation, updating the displayed set of relevant information can include determining a position associated with the user within the display (e.g., cursor position, scroll position, current active text box, followed link, etc.) as the user navigates the display, and updating the displayed set of relevant information based on the position. In examples, the position can be associated with a user navigating images (e.g., viewing, annotating, etc.) displayed within the dashboard, filling out a report within or assisted by the dashboard, and/or otherwise defined. In a first example, if a user is viewing a particular file (e.g., a prior study), S600/S601 can include displaying an option to view a report summary for the file. In a second example, S600/S601 can include displaying a set of information relevant to a specific section of a radiology report when the radiologist reaches the section.

In a second variation, updating the displayed set of relevant information can be based on an indication of a patient condition received from the user (e.g., a new finding added, a new label annotated on an image, a text section of a report filled out, etc.). In a first example, if a radiologist annotates or mentions a finding, S600/S601 can include determining information relevant to the finding. In a second example, if a radiologist indicates a differential diagnosis (through a retrieved differential diagnosis report), S600/S601 can include determining information that can help narrow the diagnosis (e.g., a patient record that indicates/contraindicates one of the differentials).

In a third variation, updating the displayed set of relevant information can be based a specific request from a user. In examples, requests can include text-based requests (e.g., written, oral, etc.), dashboard interactions (e.g., link click, button click, etc.), and/or any other inputs.

However updating the displayed set of relevant information S600/S601 can be otherwise performed.

For instance, in relation to training of models with feedback between the radiologist and a virtual assistant: if a rendered radiology output is determined to be irrelevant, the method can include blocking related radiology outputs from being retrieved and/or rendered in response to subsequent inputs of a set of inputs received. As such, the method can include: in response to determining, with the trained multimodal model, that a rendered radiology output is determined to be irrelevant, blocking radiology outputs related to the rendered radiology output from being retrieved and/or rendered in response to subsequent inputs of a set of inputs received.

Different processes and/or elements discussed above can be performed and controlled by the same or different entities. In the latter variants, different subsystems can communicate via: APIs (e.g., using API requests and responses, API keys, etc.), requests, and/or other communication channels. Communications between systems can be encrypted (e.g., using symmetric or asymmetric keys), signed, and/or otherwise authenticated or authorized.

4.7 Model Training

In relation to model architecture described, models can be trained and re-trained iteratively, using feedback loops of: input reception and processing, radiology output retrieval and rendering, followed by reception of additional inputs, where additional inputs can be used to refine the model(s) involved. Training can involve use of training data acquired from feedback loops between a virtual assistant involved in receiving inputs at the user interface of the workstation, retrieved and rendered information, followed by further inputs received by the virtual assistant. Training can further refine models involved, such that final reports that are generated using such models are automatically processed to resolve conflicts (e.g., clinically-relevant conflicts, conflicts associated with billing, etc.) and ensure consistency. As such, training can include using data derived from a conversation between the radiologist and the virtual assistant.

In specific examples, a multimodal model can be trained and re-trained (e.g., with generated outputs) using radiology output data, such as image data (e.g., from various types of images described) that has been retrieved in response to queries, paired with interactions performed at the workstation (e.g., through input devices), and corresponding free-text (e.g., radiology reports, portions of radiology reports), where the free-text can include reports generated by clinicians (e.g., radiologists) and/or modified by clinicians post-automatic generation of a candidate report. Exemplary multimodal models required orders of magnitude (e.g., 2 orders of magnitude, 3 orders of magnitude) less data to achieve similar performance in comparison to other model architecture (e.g., supervised contrastive learning models).

In variations a multimodal model can also be efficiently trained and re-trained, in comparison to training/tuning of an LLM, by way of fixing LLM and vision encoder architecture of the multimodal model and training only portions (e.g., adapter components corresponding to transformation of queries to outputs). Training can be performed using radiology inputs, such as image datasets paired with free-text clinical reports (e.g., radiology reports), leveraging routinely collected data (and not requiring manual labelling of data). Re-training can be performed using image datasets paired with automatically generated free-text clinical reports (e.g., radiology reports) that have been modified by a clinical entity (e.g., radiologist) prior to release.

Figure 6A:
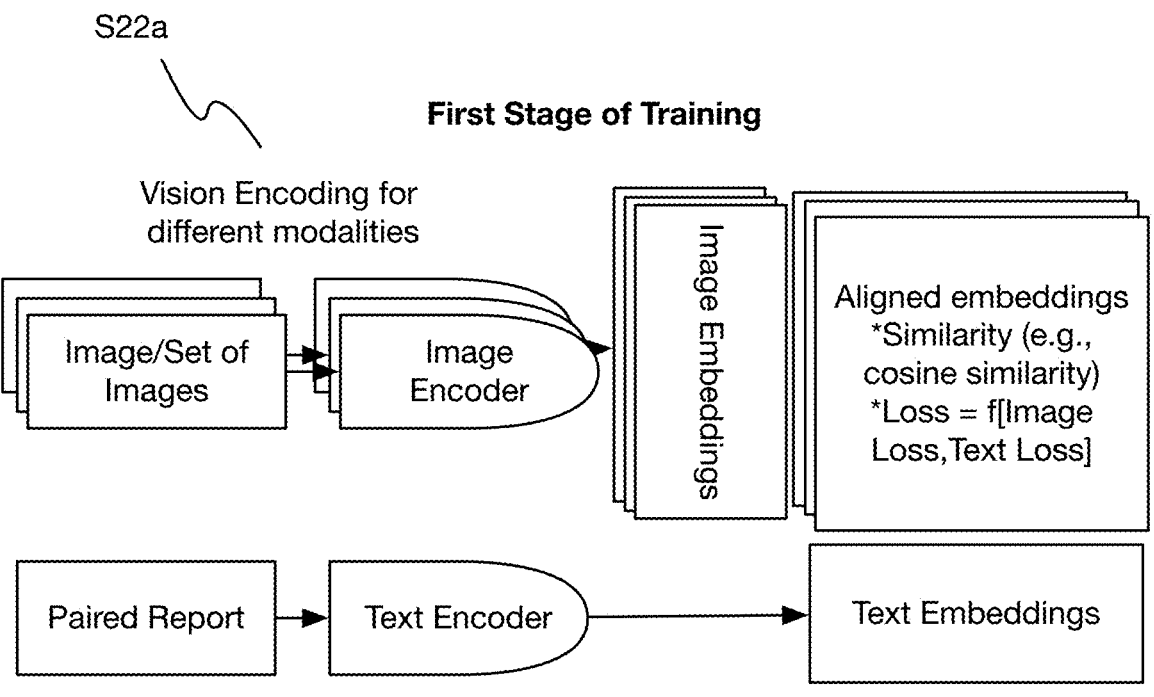
FIGS. 6A and 6B are schematics of examples of training a multimodal model associated with methods and systems for dynamic retrieval and transmission of information.
Figure 6A:
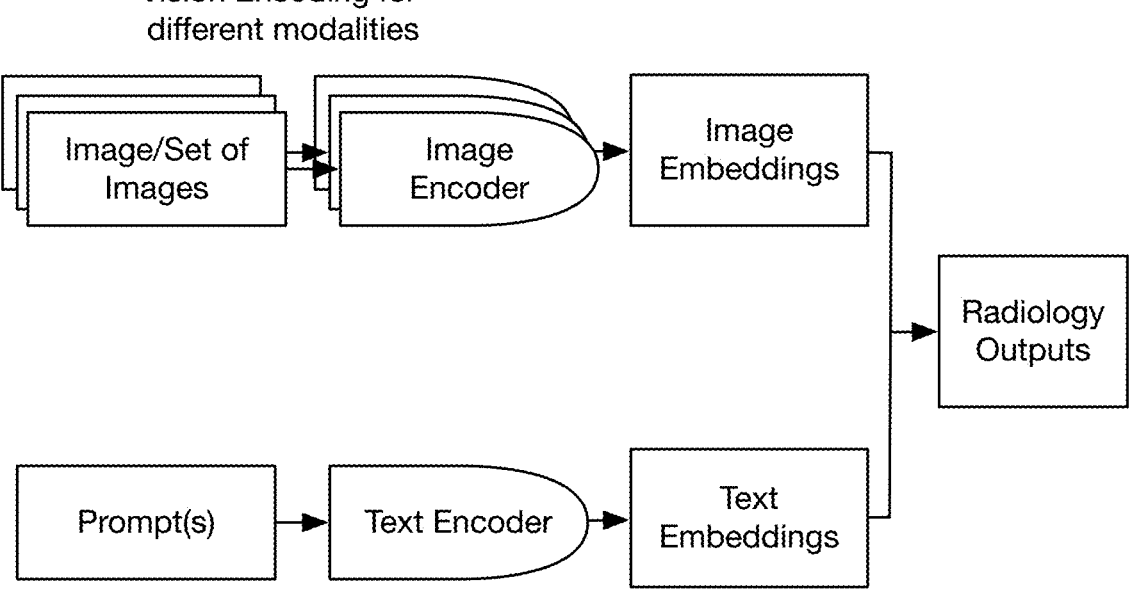

In a specific example of training, a multimodal model including vision encoder components and LLM components can be trained in stages, with co-training of the model components. In a first stage of training S22a (depicted in FIG. 6A), the multimodal model is trained using contrastive learning with language-image pre-training, a neural network approach. In the first stage of training, a training dataset including image datasets paired with free-text is processed, where by image datasets are passed as inputs to an image encoder to generate a set of image embeddings, in parallel with passing the paired free-text as inputs to a language encoder to generate a set of text embeddings. Image data can be augmented (e.g., resized, flipped, rotated, etc.) in relation to generation of image embeddings. A dataset classifier is then created from label text, and used for zero-shot prediction of test image data. Training can involve a learning rate (e.g., Stochastic gradient descent (SGD) constant learning rate was set to 0.0001, set to another value), a momentum (e.g., a momentum of 0.98, a momentum of 0.99), a number of training steps (e.g., 70,000 steps, 80,000 steps, 90,000 steps, etc.), and/or other training metrics. The first stage of training utilizes a contrastive loss function, which drives image datasets and associated returned radiology outputs (e.g., radiology reports) closer in a high-dimensional space, and drives apart mismatched image datasets and text. The first stage of training thus utilizes radiology outputs (e.g., reports, portions of reports) to align pre-trained supervised contrastive learning-based, vision-only model with a language encoder. Each encoder corresponding to a respective imaging modality can be trained independently, or together with the other encoders. Variations of training according to a first phase can additionally or alternatively involve use of a UNITER convolutional neural network model architecture, masked language model architecture, image text matching architecture, or other suitable architecture.

Figure 6B:
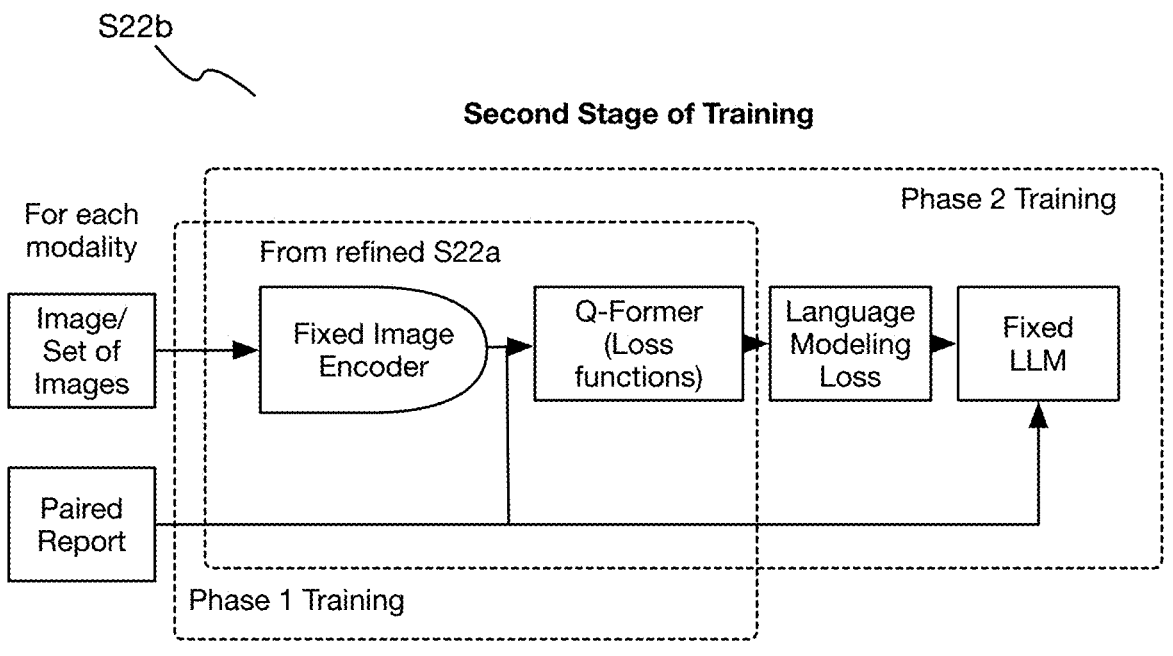
Figure 6B:
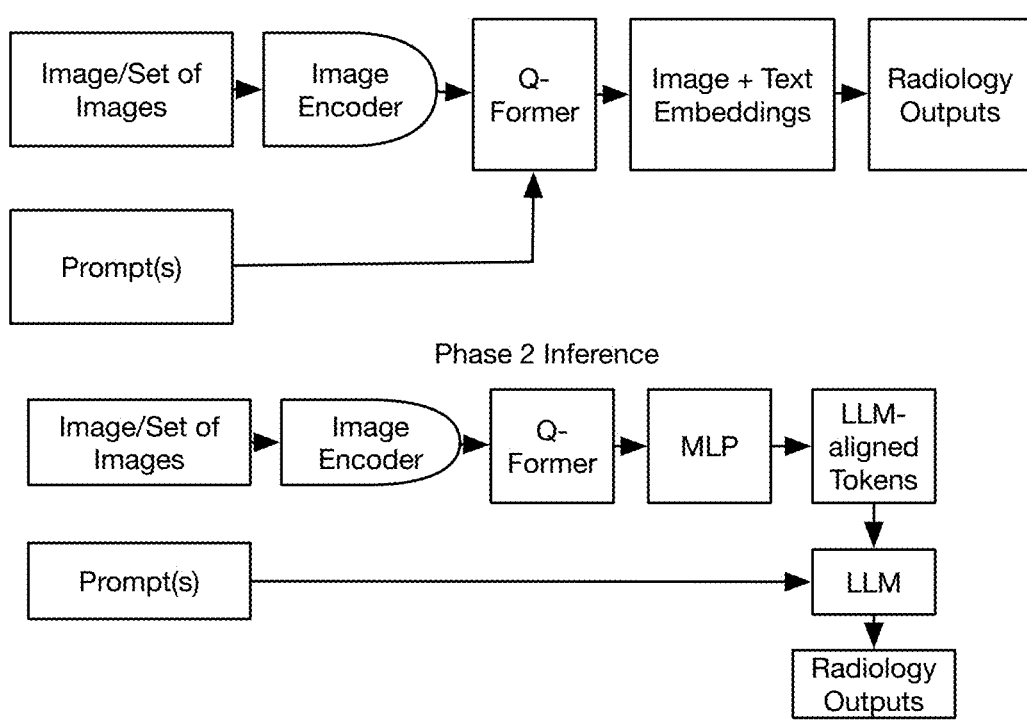

In a second stage of training S22b (depicted in FIG. 6B), the multimodal model is trained using bootstrapping language-image pre-training architecture, where a second representation of the multimodal model of the second stage of training is built directly upon a first representation of the multimodal model of the first stage of training. The second stage of training is configured to extract location-aware features from the unpooled spatial image embedding space of the first stage of training, and then to map them onto the language token space of the fixed LLM. The second representation of the multimodal model of the second stage of training functions as an adapter between the image encoder and the fixed LLM, and passes information between the image encoder(s) and the language encoder(s) of the multimodal model architecture by way of an attention mechanism. The second stage of training S22b can include multiple phases. A first phase, as shown in FIG. 6B, can involve vision-language representation learning whereby the vision-language model (e.g., Q-former) is training to understand images and reports in a shared embedding space by executing image-text contrastive learning, image-grounded text generation, and image-text matching. Standard contrastive loss can be applied for image-text contrastive learning, image-grounded text generation can be modeled as a classification problem optimized by cross-entropy loss, and image-text matching can be modeled as a binary classification problem optimized by cross-entropy loss. The resultant architecture can then extract a set of image information from image embeddings and align the set of image information with embeddings of the report text embedding space. A second phase, as shown in FIG. 6B, can involve vision-language generative learning, whereby a multilayer perceptron connecting the Q-Former with the LLM, and the Q-Former are trained to generate the radiology reports (e.g., impressions section, other sections) based upon the image embeddings from the second representation of the second stage of training. Language modeling loss is used to guide the training, and the resultant Q-Former is able to produce LLM-aligned tokens based on the image and provide the most useful information to the LLM, while removing irrelevant visual information.

Training of models can be efficiently performed by fixing all components other than the adapter, and training the adapter; however, training can alternatively be performed by further training and refining other components (e.g., encoders, image encoders, language encoders) of other portions of the multimodal model.

Evaluation of the trained multimodal model(s) can be based upon area under the receiver operating characteristic curve (AUC) metrics of classification scores for classification tasks (e.g., zero-shot classification tasks, data-efficient classification tasks, etc.). Evaluation of the trained multimodal model(s) of the set of models 110 of the system 110 can be based upon precision metrics of ranked images (e.g., based upon cosine similarity or other similarity metrics) returned in response to prompts, in relation to semantic search tasks. Evaluation of the trained multimodal model(s) of can be based upon accuracy metrics of text-generation tasks, in relation to visual question answering tasks, report quality assurance tasks, and/or other tasks.

In examples, exemplary AUC metric values for classification tasks performed using examples of described multimodal model architecture were at least 0.6, at least 0.7, at least 0.8, at least 0.89, at least 0.9, or greater for classifications related to various findings described. In examples, exemplary precision metric values for image retrieval tasks performed, involving semantic search, using examples of described multimodal model architecture were at least 0.6, at least 0.7, at least 0.8, at least 0.89, at least 0.9, or greater. In examples, exemplary accuracy metric values for text-generation tasks performed, using examples of described multimodal model architecture were at least 50%, at least 55%, at least 60%, at least 65%, at least 70%, or greater.

4.8 Executed Actions

The methods described can trigger subsequent method steps including one or more of: transmitting reports, findings, and/or other information as an input (e.g., to a report generation model, to another input determination model, etc.), displayed to a radiologist (e.g., as a reminder notification, as text that can be inserted, as analysis on what the radiologist should discuss in the report, etc.); embedding findings and/or reports directly within personal or system templates and/or macros (e.g., in a reporting platform); inserting findings and/or reports as part of a specific report type (e.g., with results of calculations automatically included in the correct location in the report); and/or other steps related to report generation, template modification, notifying relevant caretaking entities associated with involved patients.

Additionally or alternatively, the methods described can trigger subsequent method steps including: automatically triggering a downstream action; notifying and/or other establishing communications with an entity associated with the patient (e.g., to another provider, caretaker, emergency contact, establishment of a communication between two or more parties, etc.); generating and executing a referral (e.g., to a relevant specialist, to a relevant clinical trial, etc.) for the patient in response to a finding associated with a condition, where exemplary conditions are described below; providing follow-up care coordination (e.g., for one or more actionable findings) by identifying an appointment time that is suitable for the patient and a caretaker with expertise in treating the actionable finding(s); streamlining (e.g., automating) coding (e.g., for billing purposes) in relation to accurately billing suitable entities for provided care; deriving a critical results workflow; and/or performing any other suitable action.

In relation to deriving a critical results workflow as a result of finding and/or report generation, the method can include executing a critical results workflow, wherein a certain list of critical results (e.g., findings, macros, templates, etc.), which may vary by health system, radiology practice, and/or any other identifier, can automatically trigger actions (e.g., notifications within the EHR, notifications outside the EHR to an ordering and/or referring provider, etc.) for providing critical care. In particular, rapid report generation and automatic execution of a critical results workflow can provide patient care in an unprecedented manner, with respect to reduced wait times between a patient diagnostic session and treatment provision. In specific examples, the methods can initiate treatment within a duration of 4 days, within a duration of 3 days, within a duration of 2 days, within a duration of 1 day, with a duration of 8 hours, within a duration of 4 hours, within a duration of 3 hours, within a duration of 2 hours, within a duration of 1 hour, within a duration of 30 minutes, within a duration of 15 minutes, within a duration of 10 minutes, within a duration of 5 minutes, or less. In a specific example, the addition of a specific critical result (e.g., the selection of a template, the determination of a finding, the selection of a macro, etc.) associated with a certain critical condition (e.g., a pulmonary nodule) may trigger (e.g., automatically) one or more downstream actions (e.g., communications with and/or referrals to a Pulmonary clinic and/or a thoracic surgeon), with respect to a detected anomaly.

Retrieval and rendering of radiology outputs can include detecting an anomaly captured in the set of images and/or other aspect of a patient session. Variations of anomalies detected using the outputs of the multimodal models described can include global anomalies (e.g., corruptions, medical conditions, alterations, destructions) and/or local anomalies (e.g., corruptions, pathologies, local image anomalies). Variations of anomalies detected can further include image artifacts, such that the multimodal model is trained to differentiate between medically-relevant anomalies and imaging artifacts, whereby differentiation informs subsequent actions (e.g., re-image vs. medical treatment). Detection of anomalies can trigger subsequent actions, including executing imaging by another imaging modality for validation of a finding, initiating medical treatment, triggering review by a medical expert, through platform 140 described above, initiating referral to a specialist for the patient, and/or another suitable subsequent action.

Detected anomalies can be associated with one or more of: nervous system biological material (e.g., brain tissue, spinal cord tissue, nerve tissue, etc.) spanning single or multiple layers (e.g., cortical layers) of tissue and/or in relation to different types of neurons (e.g., excitatory neurons, inhibitory neurons), skeletal system biological material, muscular system biological material, respiratory system biological material, digestive system biological material, endocrine system biological material, urinary system biological material, lymphatic system biological material (e.g., spleen tissue, lymph material, tonsil tissue, etc.) spanning zone 1, zone 2, and/or zone 3 tissue, cardiovascular system biological material, integumentary system biological material, reproductive system biological material, and other biological material of a patient or subject. Anomalies can be associated with normal and diseased states, including one or more of: oncological states involving one or more of: cancer cells, circulating tumor cells, metastatic cells, benign cells, or any combination thereof.

In relation to detecting anomalies using the multimodal model described, the methods described can further include determining that an anomaly is associated with a clinical indication. The clinical condition can be a state of health, a state of disease, a pathological state, an indeterminate state, and/or another suitable state. Determining that an anomaly is associated with a clinical indication can include processing features of the anomaly, as inputs to an embodiment, variation, or example of the model(s) described, and returning a list of candidate clinical indications (e.g., ranked indications).

Upon identification of a clinical condition from the set of images, and using representations derived from the set of images as inputs to the multimodal model, the method can further include retrieving a set of candidate actions to perform based upon the clinical indication, whereby candidate actions can include actions described above, in relation to initiating and/or administering specific treatments in response to the clinical indication(s) identified.

The methods described can, however, include any other suitable processes.

5. CONCLUSIONS

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUS, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the embodiments of the invention without departing from the scope of this invention defined in the following claims.

We claim:

1. A method comprising:

Detecting, at a computing system, satisfaction of a trigger condition from an input provided by an input device used by a radiologist as a radiologist navigates a
display of a reporting platform while generating a
report, wherein the input is provided without interruption of work
by the radiologist, and wherein the trigger condition from the input involves
mouse hovering to a new section of the report within
the display, and wherein detecting satisfaction of the trigger condition
comprises detecting omission of relevant information
at a first section of the report being prepared at the
reporting platform, as the radiologist moves to a second
section of the report;

and automatically displaying relevant radiology outputs
of a set of candidate radiology outputs to the user at a
panel of the display of the reporting platform within a
duration of time less than 2 seconds after receiving the
input, wherein the relevant radiology outputs are
responsive to the trigger condition, wherein automatically displaying comprises:

a) retrieving the set of candidate radiology outputs, using
application programming interface (API) requests and
API keys involving encrypted communications
between the reporting platform and an external platform, wherein the set of candidate radiology outputs
comprises reports, laboratory tests, and images from a
medical history of a patient, upon processing the input
with a multimodal model, wherein the multimodal
model comprises an image encoder component coupled
to a large language model (LLM) component, and b) maintaining a first checklist comprising information
added to the report by the radiologist, with a matching
module of the multimodal modal, transforming the
input into a second checklist of relevant information
that should be included within the report, and displaying information that is included in the second checklist
but not included in the first checklist at the panel as the
radiologist moves to the second section of the report;
dynamically rendering the relevant radiology outputs of
the set of candidate radiology outputs at the panel; and
updating rendered radiology outputs at the panel upon
detecting further review by the radiologist of displayed
content, wherein detecting comprises monitoring
mouse movement and performing eye tracking of the
radiologist using the input device.

2. The method of claim 1, wherein the input further
comprises a text string input pertaining to a pathology of the
patient.

3. The method of claim 1, wherein retrieving the set of
candidate radiology outputs comprises retrieving a set of
digital files through the application programming interface
(API), and modifying the set of digital files prior to rendering relevant radiology outputs at the display.

4. The method of claim 3, wherein the set of candidate
radiology outputs comprises a differential diagnosis report
for the patient.

5. The method of claim 1, wherein the set of candidate
radiology outputs comprises a test panel result providing a
clinical context associated with at least one of the set of
inputs.

6. The method of claim 1, further comprising processing
the set of candidate radiology outputs prior to rendering
relevant radiology outputs at the panel, wherein processing
comprises cropping, adjusting resolution of, and positioning
a candidate radiology output within the panel during rendering.

7. The method of claim 1, further comprising training the
multimodal model-to generate a trained multimodal model.

8. The method of claim 7, wherein training the multimodal model comprises training the multimodal model with
data derived from a conversation between the radiologist
and the virtual assistant.

9. The method of claim 7, wherein the wherein the image
encoder component is coupled to the LLM component with
an adapter structured to pass information between the image
encoder component and the LLM component with an attention mechanism.

10. The method of claim 9, further comprising re-training
the multimodal model, wherein re-training the multimodal
model comprises training only the adapter and fixing all
other components of the multimodal model.

11. The method of claim 7, wherein training the multimodal model comprises training with contrastive learning
comprising a contrastive loss function.

12. The method of claim 7, further comprising: in
response to determining, with the trained multimodal model,
that a rendered radiology output is determined to be irrelevant, blocking radiology outputs related to the rendered
radiology output from being retrieved in response to reception of subsequent inputs from the radiologist.

13. The method of claim 1, wherein dynamically rendering relevant radiology outputs comprises ranking the set of
candidate radiology outputs upon determining values of a
relevancy metric for each of the set of candidate radiology
outputs, and wherein rendering relevant radiology outputs
comprises replacing a previously-rendered radiology output
from the panel in response to receiving the set of inputs.

14. The method of claim 1, wherein the input comprises
a cursor movement and an eye tracking system input,
wherein dynamically rendering relevant radiology outputs
of the set of candidate radiology outputs comprises:

detecting a region of an image being reviewed by the
radiologist at the display, from the cursor movement
and the eye tracking system input, retrieving a summarization of findings from a prior report
for the patient within the panel using the multimodal
model based on detection of the region, and updating rendered information from the summarization of
findings at the panel, thereby facilitating the radiologist
in preparation of the report.

15. A method comprising:

detecting, at a computing system, satisfaction of a trigger
condition from an input provided by an input device
used by a radiologist as the radiologist navigates a
display of a reporting platform while generating a
report, wherein the input is provided without interruption of work
by the radiologist, and wherein the trigger condition from the input involves
mouse hovering to a new section of the report within
the display, and wherein detecting satisfaction of the trigger condition
comprises detecting omission of relevant information
at a first section of the report being prepared at the
reporting platform, as the radiologist moves to a second
section of the report;

and automatically rendering relevant radiology outputs of
a set of candidate radiology outputs to the user at a
panel of the display of the reporting platform within a
duration of time less than 2 seconds after receiving the
input, wherein the relevant radiology outputs are
responsive to the trigger condition, wherein automatically rendering comprises:

a) retrieving a set of candidate radiology outputs, using application programming interface (API) requests and API keys involving encrypted communications between the reporting platform and an external platform, wherein the set of candidate radiology outputs comprises reports, laboratory tests, and images from a medical history of a patient, upon processing the input with a multimodal model comprising an image encoder component coupled to a large language model (LLM) component, and b) maintaining a first checklist comprising information added to the report by the radiologist, with a matching module of the multimodal modal, transforming the input into a second checklist of relevant information that should be included within the report, and displaying information that is included in the second checklist but not included in the first checklist at the panel as the radiologist moves to the second section of the report;

dynamically rendering, at the panel of the display, relevant radiology outputs of the set of candidate radiology outputs, wherein the relevant radiology outputs comprise images and corresponding free-text derived from radiology reports returned as outputs from the multimodal model;

updating rendered radiology outputs at the panel upon detecting further review by the radiologist of displayed content, wherein detecting comprises monitoring mouse movement and performing eye tracking of the radiologist using the input device;

with the multimodal model, detecting an anomaly present in the set of candidate radiology outputs;

with the multimodal model, determining that the anomaly is one of a medically-relevant anomaly and an imaging artifact; and upon detection of the anomaly, triggering re-imaging of the patient using an imaging modality for validation of a finding associated with the anomaly.

16. The method of claim 15, wherein the set of candidate radiology outputs comprises a set of annotated images from historical radiology reports, and a differential diagnosis report.

17. The method of claim 15, further comprising rendering an updated set of relevant radiology outputs at the panel of the display of the reporting platform, the updated set of relevant radiology outputs retrieved using the multimodal model, as a position within the display is adjusted using the input device, wherein the position is associated with a section of a radiology report, and wherein rendering the updated set of relevant radiology outputs comprises retrieving a radiology image relevant to the section of a radiology report, through encrypted communications with a Picture Archiving and Communication System (PACS).

* * * * *